United States Patent
Li

(10) Patent No.: US 11,046,782 B2
(45) Date of Patent: Jun. 29, 2021

(54) METHODS FOR TREATMENT AND DIAGNOSIS OF CANCER BY TARGETING GLYCOPROTEIN A REPETITIONS PREDOMINANT (GARP) AND FOR PROVIDING EFFECTIVE IMMUNOTHERAPY ALONE OR IN COMBINATION

(71) Applicant: MUSC FOUNDATION FOR RESEARCH DEVELOPMENT, Charleston, SC (US)

(72) Inventor: Zihai Li, Mount Pleasant, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 115 days.

(21) Appl. No.: 16/089,498

(22) PCT Filed: Mar. 30, 2017

(86) PCT No.: PCT/US2017/025037
§ 371 (c)(1),
(2) Date: Sep. 28, 2018

(87) PCT Pub. No.: WO2017/173091
PCT Pub. Date: Oct. 5, 2017

(65) Prior Publication Data
US 2019/0127483 A1 May 2, 2019

Related U.S. Application Data

(60) Provisional application No. 62/315,069, filed on Mar. 30, 2016, provisional application No. 62/315,121, filed on Mar. 30, 2016.

(51) Int. Cl.
| | |
|---|---|
| *C07K 16/34* | (2006.01) |
| *C07K 16/30* | (2006.01) |
| *C07K 16/28* | (2006.01) |
| *A61P 35/00* | (2006.01) |
| *A61K 9/00* | (2006.01) |
| *A61K 31/675* | (2006.01) |
| *A61K 31/7076* | (2006.01) |
| *A61K 45/06* | (2006.01) |
| *A61K 39/395* | (2006.01) |
| *A61K 39/00* | (2006.01) |

(52) U.S. Cl.
CPC .............. *C07K 16/34* (2013.01); *A61K 9/00* (2013.01); *A61K 9/0019* (2013.01); *A61K 31/675* (2013.01); *A61K 31/7076* (2013.01); *A61K 39/39558* (2013.01); *A61K 45/06* (2013.01); *A61P 35/00* (2018.01); *C07K 16/28* (2013.01); *C07K 16/2827* (2013.01); *C07K 16/2866* (2013.01); *C07K 16/30* (2013.01); *C07K 16/3015* (2013.01); *C07K 16/3046* (2013.01); *A61K 2039/505* (2013.01); *C07K 2317/33* (2013.01); *C07K 2317/76* (2013.01)

(58) Field of Classification Search
CPC ........ C07K 16/34; C07K 16/28; C07K 16/30; A61P 35/00; A61K 9/00
USPC ....................................................... 424/139.1
See application file for complete search history.

(56) References Cited

U.S. PATENT DOCUMENTS

| | | |
|---|---|---|
| 5,242,810 A | 9/1993 | Maraganore et al. |
| 2003/0134341 A1 | 7/2003 | Gruenberg |
| 2003/0175272 A1 | 9/2003 | Gruenberg |
| 2004/0180812 A1 | 9/2004 | Dicker et al. |
| 2009/0280116 A1 | 11/2009 | Smith et al. |
| 2010/0092491 A1 | 4/2010 | Anastasi et al. |
| 2010/0115639 A1 | 5/2010 | Goetsch |
| 2010/0278842 A1 | 11/2010 | Mao et al. |
| 2012/0082667 A1 | 4/2012 | Yokoseki et al. |
| 2012/0195831 A1 | 8/2012 | Zhang et al. |
| 2014/0199301 A1 | 7/2014 | Erdag et al. |
| 2015/0337034 A1 | 11/2015 | Schurpf et al. |

FOREIGN PATENT DOCUMENTS

| | | |
|---|---|---|
| WO | WO 2019/018632 | 1/1919 |
| WO | WO 2012/034061 | 3/2012 |
| WO | WO 2014/087240 | 6/2014 |
| WO | WO 2015/015003 | 2/2015 |

OTHER PUBLICATIONS

Cuende et al., "Monoclonal antibodies against GARP/TGF-beta1 complexes inhibit the immunosuppressive activity of human regulatory T cells in vivo," *Science Translational Medicine*, 7(284):284ra56-284ra56, 2015.
Extended European Search Report issued in European Patent Application No. 17776655.7, dated Oct. 24, 2019.
PCT International Search Report and Written Opinion issued in International Application No. PCT/US17/25037, dated Aug. 29, 2017.
PCT International Search Report and Written Opinion issued in International Application No. PCT/US2018/042873, dated Nov. 15, 2018.
PCT Invitation to Pay Additional Fees issued in International Application No. PCT/US2018/042873, dated Sep. 21, 2018.
Vermeersch et al., The role of platelet and endothelial GARP in thrombosis and hemostasis, *PLoS One*, 12(3):e0173329, pp. 1-18, 2017.

*Primary Examiner* — Yan Xiao
(74) *Attorney, Agent, or Firm* — Parker Highlander PLLC

(57) ABSTRACT

Isolated or recombinant monoclonal antibodies that bind to GARP are provided. In some cases, antibodies of the embodiments can be used for the detection, diagnosis and/or therapeutic treatment of human diseases, such as cancer. Further provided herein are methods and compositions for treating cancer in an individual comprising administering to the individual an effective amount of an anti-platelet agent and a T cell therapy.

2 Claims, 13 Drawing Sheets
Specification includes a Sequence Listing.

SEQUENCE LISTING

```
<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Gly Tyr Ser Ile Thr Ser Asp Tyr Ala
1               5

<210> SEQ ID NO 2
<211> LENGTH: 7
<212> TYPE: PRT
<213> ORGANISM: Homo sapiens

<400> SEQUENCE: 2

Ile Ser Tyr Ser Gly Ser Thr
1               5

<210> SEQ ID NO 3
<211> LENGTH: 18
<212> TYPE: PRT
<213> ORGANISM: Homo sapiens

<400> SEQUENCE: 3

Ala Lys Ser Gly Gly Asp Tyr Tyr Gly Ser Ser Ser Tyr Trp Tyr Phe
1               5                   10                  15

Asp Val

<210> SEQ ID NO 4
```

-continued

```
<211> LENGTH: 126
<212> TYPE: PRT
<213> ORGANISM: Homo sapiens

<400> SEQUENCE: 4

Leu Asp Val Gln Leu Gln Glu Ser Gly Pro Gly Leu Val Lys Pro Ser
1               5                   10                  15

Gln Ser Leu Ser Leu Thr Cys Thr Val Thr Gly Tyr Ser Ile Thr Ser
            20                  25                  30

Asp Tyr Ala Trp Asn Trp Ile Arg Gln Phe Pro Gly Asn Lys Leu Glu
        35                  40                  45

Trp Met Gly Tyr Ile Ser Tyr Ser Gly Ser Thr Ser Tyr Thr Pro Ser
    50                  55                  60

Leu Lys Ser Arg Ile Ser Ile Thr Arg Asp Thr Ser Lys Asn His Phe
65                  70                  75                  80

Phe Leu Gln Ser Asn Ser Val Thr Thr Glu Asp Thr Ala Thr Tyr Tyr
                85                  90                  95

Cys Ala Lys Ser Gly Gly Asp Tyr Tyr Gly Ser Ser Tyr Trp Tyr
            100                 105                 110

Phe Asp Val Trp Gly Ala Gly Thr Thr Val Thr Val Ser Ser
        115                 120                 125

<210> SEQ ID NO 5
<211> LENGTH: 12
<212> TYPE: PRT
<213> ORGANISM: Homo sapiens

<400> SEQUENCE: 5

Gln Ser Leu Leu Asn Ser Arg Ser Gln Lys Asn Tyr
1               5                   10

<210> SEQ ID NO 6
<211> LENGTH: 3
<212> TYPE: PRT
<213> ORGANISM: Homo sapiens

<400> SEQUENCE: 6

Arg Ala Ser
1

<210> SEQ ID NO 7
<211> LENGTH: 9
<212> TYPE: PRT
<213> ORGANISM: Homo sapiens

<400> SEQUENCE: 7

Gln Asn Asp His Ser Tyr Pro Phe Thr
1               5

<210> SEQ ID NO 8
<211> LENGTH: 113
<212> TYPE: PRT
<213> ORGANISM: Homo sapiens

<400> SEQUENCE: 8

Asp Ile Gln Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Arg Ser Gln Lys Asn Tyr Leu Ala Trp Tyr Gln Gln Lys Pro Gly Gln
        35                  40                  45
```

-continued

```
Pro Pro Lys Leu Leu Ile Tyr Arg Ala Ser Thr Arg Gly Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp His Ser Tyr Pro Phe Thr Phe Gly Ser Gly Thr Lys Leu Glu Ile
            100                 105                 110

Lys

<210> SEQ ID NO 9
<211> LENGTH: 8
<212> TYPE: PRT
<213> ORGANISM: Homo sapiens

<400> SEQUENCE: 9

Gly Phe Thr Phe Ser Asn Tyr Val
 1               5

<210> SEQ ID NO 10
<211> LENGTH: 8
<212> TYPE: PRT
<213> ORGANISM: Homo sapiens

<400> SEQUENCE: 10

Ile Ser Ser Gly Gly Ser Tyr Thr
 1               5

<210> SEQ ID NO 11
<211> LENGTH: 13
<212> TYPE: PRT
<213> ORGANISM: Homo sapiens

<400> SEQUENCE: 11

Ala Arg Gly Tyr Asp Asn Gly Asp Tyr Val Met Asp Tyr
 1               5                  10

<210> SEQ ID NO 12
<211> LENGTH: 120
<212> TYPE: PRT
<213> ORGANISM: Homo sapiens

<400> SEQUENCE: 12

Glu Val Lys Leu Val Glu Ser Gly Gly Ser Val Lys Pro Gly Gly
 1               5                  10                  15

Ser Leu Lys Leu Ser Cys Ala Ala Ser Gly Phe Thr Phe Ser Asn Tyr
                 20                  25                  30

Val Met Ser Trp Val Arg Gln Thr Pro Glu Lys Arg Leu Glu Trp Val
             35                  40                  45

Ala Thr Ile Ser Ser Gly Gly Ser Tyr Thr Tyr Pro Asp Ser Val
         50                  55                  60

Lys Gly Arg Leu Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Ala Arg Gly Tyr Asp Asn Gly Asp Tyr Val Met Asp Tyr Trp Gly Gln
            100                 105                 110

Gly Thr Ser Val Thr Val Ser Ser
            115                 120
```

<210> SEQ ID NO 13
<211> LENGTH: 10
<212> TYPE: PRT
<213> ORGANISM: Homo sapiens

<400> SEQUENCE: 13

Glu Ser Val Asp Thr Tyr Gly Asn Ser Phe
1               5                   10

<210> SEQ ID NO 14
<211> LENGTH: 3
<212> TYPE: PRT
<213> ORGANISM: Homo sapiens

<400> SEQUENCE: 14

Arg Ala Ser
1

<210> SEQ ID NO 15
<211> LENGTH: 9
<212> TYPE: PRT
<213> ORGANISM: Homo sapiens

<400> SEQUENCE: 15

Gln Gln Thr Asn Glu His Pro Pro Thr
1               5

<210> SEQ ID NO 16
<211> LENGTH: 111
<212> TYPE: PRT
<213> ORGANISM: Homo sapiens

<400> SEQUENCE: 16

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Tyr
            20                  25                  30

Gly Asn Ser Phe Met His Trp Tyr Gln Gln Ile Pro Gly Gln Pro Pro
        35                  40                  45

Lys Val Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Gly Asp Val Ala Thr Tyr Tyr Cys Gln Gln Thr Asn
                85                  90                  95

Glu His Pro Pro Thr Phe Gly Gly Gly Thr Lys Leu Glu Ile Lys
            100                 105                 110

<210> SEQ ID NO 17
<211> LENGTH: 12
<212> TYPE: PRT
<213> ORGANISM: Homo sapiens

<400> SEQUENCE: 17

Leu Arg Thr Leu Ser Leu Glu Asn Ser Leu Thr Arg
1               5                   10

METHODS FOR TREATMENT AND DIAGNOSIS OF CANCER BY TARGETING GLYCOPROTEIN A REPETITIONS PREDOMINANT (GARP) AND FOR PROVIDING EFFECTIVE IMMUNOTHERAPY ALONE OR IN COMBINATION

The present application is a national phase application under 35 U.S.C. § 371 of International Application No. PCT/US2017/025037, filed Mar. 30, 2017, which claims the priority benefit of U.S. Provisional Application Nos. 62/315,069 and 62/315,121, both of which were filed Mar. 30, 2016, the entire contents of which are being hereby incorporated by reference.

The invention was made with Government support under Grant Nos. R01AI070603, P01CA186866, R01CA188419, and P30CA138313 awarded by the National Institutes of Health. The Government has certain rights in the invention.

INCORPORATION OF SEQUENCE LISTING

Pursuant to 37 C.F.R. 1.821(c), a sequence listing is submitted herewith as an ASCII compliant text file named "MESCP0096US_ST25.txt", created on Sep. 25, 2018 and having a size of ~7 kilobytes. The content of the aforementioned file is hereby incorporated by reference in its entirety.

BACKGROUND OF THE INVENTION

1. Field of the Invention

The present invention relates generally to the fields of cancer biology, immunology and medicine. More particularly, it concerns GARP (Glycoprotein-A Repetitions Predominant Protein) targeting monoclonal antibodies for the treatment and detection of cancer, and methods of treating cancer using immunotherapy. Specifically, a method of treating cancer by combining T cell therapy with an anti-platelet agent is provided.

2. Description of Related Art

TGF-β is a pleiotropic cytokine widely expressed in most tissues. Aberrance in its signaling has been implicated in multiple diseases and cancer in particular (Derynck et al., 2001; Massague, 2008). In addition to growth arrest, TGF-β induces a variety of malignant cellular phenotypes including invasion, loss of cellular adhesion, epithelial-mesenchymal transition and metastasis (Bhowmick et al., 2001; Derynck et al., 2001; Oft et al., 1998). Importantly, the role of TGF-β in shaping the tumor micro-environment is a critical aspect of its function in carcinogenesis. For example, TGF-β1 is a potent inducer of angiogenesis (Roberts et al., 1986), either directly by inducing VEGF expression (Pertovaara et al., 1994) or by recruiting other cells such as monocytes which in turn secrete pro-angiogenic molecules (Sunderkotter et al., 1991). TGF-β can also manipulate the tumor micro-environment by favoring the evasion of cancer cells from immune-surveillance, via tampering the effective antitumor functions of T cells, NK cells, B cells or others (Kehrl et al., 1986; Kopp et al., 2009), through its direct effect as well as its ability to induce Foxp3$^+$ regulatory T cells (Li and Flavell, 2008).

Biochemically, TGF-β exists in at least 4 different forms: 1) freely soluble active TGF-β; 2) soluble TGF-β associated with latency associated peptide or LAP (forming a TGF-β-LAP complex, known as latent TGF-β or LTGF-(β); 3) LTGF-β associated covalently with large TGF-β-binding protein (LTBP), thus forming the TGF-β-LAP-LTBP complex; and 4) the membrane latent form of TGF-β (mTGF-β) (Li and Flavell, 2008; Tran, 2012). Only LAP-free TGF-β is known to be biologically active. Therefore, a large pool of TGF-β is sequestered in the extracellular matrix in a latent form before being activated by proteases such as MMP2, MMP9 and plasmin (Lyons et al., 1990; Sato and Rifkin, 1989; Yu and Stamenkovic, 2000), which are in turn secreted by tumor cells and other cells in the tumor microenvironment. mLTGF-β is expressed by two hematopoietic cell types; platelets and regulatory T cells in association with the transmembrane protein Glycoprotein A Repetitions Predominant (GARP), also known as leucine-rich repeat containing 32 (LRRC32) (Tran et al., 2009; Wang et al., 2012). Besides its role as mLTGF-β docking receptor, GARP is critical for regulating TGFβ activation and bioavailability: GARP enhances proTGF-β maturation and cooperates with integrins in mLTGF-β activation (Wang et al., 2012). The potential role of GARP in cancer is described herein.

Passive immunization through the adoptive transfer of a large number of tumor-reactive lymphocytes, known as adoptive cell therapy (ACT) is currently the most effective treatment for patients with metastatic melanoma, and is extensively explored for the treatment of other human cancers. ACT involves the administration of large numbers of highly selective cells with high avidity for tumor antigens. These T cells can be programmed and activated ex vivo to exhibit antitumor effector functions. Furthermore, T cell infusion may be preceded by 'conditioning' of the patient with lymphodepleting chemotherapy or total body irradiation, which enables the diminution of immunosuppressive cell types/factors followed by the infusion of tumor-specific T cells. Although ACT appears to be promising in many aspects, extensive works needs to be done in order for the treatment to be more successful.

The encouraging clinical achievements of ACT are confronted with major obstacles which limit the clinical benefit and broader application of this approach. Whereas some of the intrinsic difficulties are attributable to the particular method employed for isolation, propagation or generation of the effector lymphocytes, others, such as the exhaustion of the proliferative and survival potential of fully differentiated T cells, seem to be a more general phenomena related to the effector phenotype. Other difficulties arise from extrinsic suppressive mechanisms exerted at the tumor site, which are mediated either by direct cell-to-cell contact with tumor cells, stromal cells and regulatory T cells (Tregs), or by inhibitory cytokines such as TGF-β. As a result, the administered T cells exhibit decreased intratumoral persistence and impaired functionality, and often fall short from executing a detectable tumoricidal effect. Thus, there is a need for methods to evade or subvert these suppressive mechanisms and augment the curative outcome of ACT.

SUMMARY OF THE INVENTION

Embodiments of the present disclosure provide methods for the treatment of cancer. In a first embodiment, there is provided an isolated monoclonal antibody, wherein the antibody specifically binds to GARP and wherein the antibody competes for binding of the GARP epitopes with a 4d3 or 5c5 monoclonal antibody. In some aspects, the antibody comprises (a) a first $V_H$ CDR at least 80% identical to $V_H$ CDR1 of 4d3 (SEQ ID NO: 1) or 5c5 (SEQ ID NO: 9); (b) a second $V_H$ CDR at least 80% identical to $V_H$ CDR2 of 4d3

(SEQ ID NO: 2) or 5c5 (SEQ ID NO: 10); (c) a third $V_H$ CDR at least 80% identical to $V_H$ CDR3 of 4d3 (SEQ ID NO: 3) or 5c5 (SEQ ID NO: 11); (d) a first $V_L$ CDR at least 80% identical to $V_L$ CDR1 of 4d3 (SEQ ID NO: 5) or 5c5 (SEQ ID NO: 13); (e) a second $V_L$ CDR at least 80% identical to $V_L$ CDR2 of 4d3 (SEQ ID NO: 6) or 5c5 (SEQ ID NO: 14); and (f) a third $V_L$ CDR at least 80% identical to $V_L$ CDR3 of 4d3 (SEQ ID NO: 7) or 5c5 (SEQ ID NO: 15).

In certain aspects, the antibody comprises a first $V_H$ CDR at least 80% identical to SEQ ID NO: 1, a second $V_H$ CDR at least 80% identical to SEQ ID NO: 2, a third $V_H$ CDR at least 80% identical to SEQ ID NO: 3, a first $V_L$ CDR at least 80% identical to SEQ ID NO: 5, a second $V_L$ CDR at least 80% identical to SEQ ID NO: 6, and a third $V_L$ CDR at least 80% identical to SEQ ID NO: 7. In a specific aspect, the antibody comprises a first $V_H$ CDR is identical to SEQ ID NO: 1, a second $V_H$ CDR is identical to SEQ ID NO: 2, a third $V_H$ CDR is identical to SEQ ID NO: 3, a first $V_L$ CDR is identical to SEQ ID NO: 5, a second $V_L$ CDR is identical to SEQ ID NO: 6, and a third $V_L$ CDR is identical to SEQ ID NO: 7.

In other aspects, the antibody comprises a first $V_H$ CDR at least 80% identical to SEQ ID NO: 9, a second $V_H$ CDR at least 80% identical to SEQ ID NO: 10, a third $V_H$ CDR at least 80% identical to SEQ ID NO: 11, a first $V_L$ CDR at least 80% identical to SEQ ID NO: 13, a second $V_L$ CDR at least 80% identical to SEQ ID NO: 14, and a third $V_L$ CDR at least 80% identical to SEQ ID NO: 15. In a particular aspect, the antibody comprises a first $V_H$ CDR is identical to SEQ ID NO: 9, a second $V_H$ CDR is identical to SEQ ID NO: 10, a third $V_H$ CDR is identical to SEQ ID NO: 11, a first $V_L$ CDR is identical to SEQ ID NO: 13, a second $V_L$ CDR is identical to SEQ ID NO: 14, and a third $V_L$ CDR is identical to SEQ ID NO: 15.

In some aspects, the antibody comprises (i) a $V_H$ domain at least about 80% identical to the $V_H$ domain of 4d3 (SEQ ID NO: 4) and a $V_L$ domain at least about 80% identical to the $V_L$ domain of 4d3 (SEQ ID NO: 8); or (ii) a $V_H$ domain at least about 80% identical to the $V_H$ domain of 5c5 (SEQ ID NO: 12) and a $V_L$ domain at least about 80% identical to the $V_L$ domain of 5c5 (SEQ ID NO: 16). In a specific aspect, the antibody comprises a $V_H$ domain identical to the $V_H$ domain of 4d3 (SEQ ID NO: 4) and a $V_L$ domain identical to the $V_L$ domain of 4d3 (SEQ ID NO: 8). In another particular aspect, the antibody comprises a $V_H$ domain identical to the $V_H$ domain of 5c5 (SEQ ID NO: 12) and a $V_L$ domain identical to the $V_L$ domain 5c5 (SEQ ID NO: 16). In one specific aspect, the antibody is the 4d3 or 5c5 antibody. In further aspects, the antibody is recombinant.

In additional aspects, the antibody is an IgG, IgM, IgA or an antigen binding fragment thereof. In certain aspects, the antibody is a Fab', a F(ab')2, a F(ab')3, a monovalent scFv, a bivalent scFv, or a single domain antibody. In specific aspects, the antibody may be a human, humanized antibody or de-immunized antibody. In some aspects, the antibody is conjugated to an imaging agent, a chemotherapeutic agent, a toxin or a radionuclide. In certain aspects, the antibody has at least second binding specificity, such as a bispecific antibody that binds to GARP and a second target.

A further embodiment of the invention provides a composition comprising an antibody of the embodiments and aspects described herein in a pharmaceutically acceptable carrier.

In still a further embodiment, the invention provides an isolated polynucleotide molecule comprising a nucleic acid sequence encoding an antibody of the embodiments and aspects described herein.

Yet still a further embodiment provides a recombinant polypeptide comprising an antibody $V_H$ domain comprising CDRs 1-3 of the $V_H$ domain of 4d3 (SEQ ID NOs: 1, 2, and 3); CDRs 1-3 of the $V_H$ domain of 5c5 (SEQ ID NOs: 9, 10, and 11).

In still a further embodiment, there is provided a recombinant polypeptide comprising an antibody $V_L$ domain comprising CDRs 1-3 of the $V_L$ domain of 4d3 (SEQ ID NOs: 5, 6, and 7); or 5c5 (SEQ ID NOs: 13, 14, and 15).

Another further embodiment provides an isolated polynucleotide molecule comprising a nucleic acid sequence encoding a polypeptide of the embodiments and aspects described herein.

In still yet a further embodiment, the invention provides a host cell comprising one or more polynucleotide molecule(s) encoding an antibody of the embodiments or a recombinant polypeptide of the embodiments and aspects described herein. In some aspects, the host cell is a mammalian cell, a yeast cell, a bacterial cell, a ciliate cell or an insect cell.

Yet a further embodiment of the invention provides a method of manufacturing an antibody comprising (a) expressing one or more polynucleotide molecule(s) encoding a $V_L$ and $V_H$ chain of an antibody of the embodiments in a cell; and (b) purifying the antibody from the cell.

In a further embodiment, the invention provides a method for treating a subject having a cancer comprising administering an effective amount of an antibody of any one of the embodiments and aspects described herein. In certain aspects, the cancer is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In particular aspects, the antibody is in a pharmaceutically acceptable composition. In some specific aspects, the antibody is administered systemically. In other aspects, the antibody is administered intravenously, intradermally, intratumorally, intramuscularly, intraperitoneally, subcutaneously, or locally. In further aspects, the method additionally comprises administering at least a second anticancer therapy to the subject. In some of these aspects, the second anticancer therapy is a surgical therapy, chemotherapy, radiation therapy, cryotherapy, hormonal therapy, immunotherapy or cytokine therapy.

Yet still a further embodiment of the invention provides a method for detecting a cancer in a subject comprising testing for the presence of elevated GARP relative to a control in a sample from the subject, wherein the testing comprises contacting the sample with an antibody of any of the embodiments and aspects described herein. In some aspects, the method is further defined as an in vitro method.

In still a further embodiment, there is provided an isolated antibody, wherein the antibody comprises a first $V_H$ CDR at least 80% identical to $V_H$ CDR1 of 4d3 (SEQ ID NO: 1) or 5c5 (SEQ ID NO: 9), a second $V_H$ CDR at least 80% identical to $V_H$ CDR2 of 4d3 (SEQ ID NO: 2) or 5c5 (SEQ ID NO: 10), a third $V_H$ CDR at least 80% identical to $V_H$ CDR3 of 4d3 (SEQ ID NO: 3) or 5c5 (SEQ ID NO: 11), a first $V_L$ CDR at least 80% identical to $V_L$ CDR1 of 4d3 (SEQ ID NO: 5) or 5c5 (SEQ ID NO: 13), a second $V_L$ CDR at least 80% identical to $V_L$ CDR2 of 4d3 (SEQ ID NO: 6) or 5c5 (SEQ ID NO: 14), and a third $V_L$ CDR at least 80% identical to $V_L$ CDR3 of 4d3 (SEQ ID NO: 7) or 5c5 (SEQ ID NO: 15).

In another embodiment, there is provided a method of treating cancer in a subject comprising administering an immunotherapy in combination with an anti-platelet agent. In some aspects, a method for treating a subject involves administering a T-cell, NK-cell, NKT-cell therapy, immune checkpoint inhibitor (e.g., an antibody), cytokine, oncolytic or immune stimulating therapy (e.g., a vaccine) in combination with an anti-platelet agent. In some aspects, said subject is a human subject.

In some aspects, the T cell therapy comprises administration of tumor infiltrating lymphocytes (TILs), CD8$^+$ T cells and/or CD4$^+$ T cells. In certain aspects, the T cell therapy comprises administration of tumor-specific T cells. In some aspects, the tumor-specific T cells are autologous. In certain aspects, the tumor-specific T cells are engineered to express a T cell receptor (TCR) or chimeric antigen receptor (CAR) receptor having antigenic specificity for GARP or a tumor antigen. For example, the tumor-antigen is selected from the group consisting of tEGFR, Her2, CD19, CD20, CD22, mesothelin, CEA, CD23, CD24, CD30, CD33, CD38, CD44, EGFR, EGP-2, EGP-4, EPHa2, ErbB2, FBP, MAGE-A1, MUC1, NY-ESO-1, and MART-1. In certain aspects, the CAR comprises co-stimulatory molecule endodomains selected from the group consisting of CD28, CD27, 4-IBB, OX40 ICOS, and a combination thereof.

In some aspects, the method further comprises lymphodepletion of the subject prior to administration of the T cell therapy. For example, lymphodepletion comprises administration of cyclophosphamide, fludarabine and/or irradiation (e.g., low dose of total body irradiation).

In particular aspects, the anti-platelet agent is an anti-GARP antibody or fragment thereof. For example, the anti-GARP antibody is a monoclonal antibody. In some aspects, the anti-GARP antibody is a human, humanized antibody or de-immunized antibody. In certain aspects, the anti-GARP antibody comprises the CDR sequences of the 4d3 or 5c5 antibody.

In other aspects, the anti-platelet agent is not an anti-GARP antibody. In some aspects, the anti-platelet agent is selected from the group consisting of a cyclooxygenase inhibitor, adenosine diphosphate (ADP) inhibitor, phosphodiesterase inhibitor, protease-activated receptor-1 (PAR-1) antagonist such as thrombin inhibitor, glycoprotein IIB/IIIA inhibitor, adenosine reuptake inhibitor, and thromboxane inhibitor. For example, the ADP inhibitors include clopidogrel, prasugrel, or ticlopidine.

In some aspects, the method further comprises administering at least one additional therapeutic agent. In certain aspects, the at least one additional therapeutic agent is chemotherapy, immunotherapy, surgery, radiotherapy, or biotherapy. For example, the at least one additional therapeutic agent is a TGFβ inhibitor. In some aspects, the TGFβ inhibitor is Galunisertib (LY2157299), trabedersen, fresolimumab, LY2382770, lucanix, or PF-03446962. In certain aspects, the immunotherapy is an immune checkpoint inhibitor. For example, the at least one immune checkpoint inhibitor is an anti-CTLA-4 antibody. In some aspects, the immune checkpoint inhibitor is a human programmed cell death 1 (PD-1) binding antagonist, a PDL1 binding antagonist ore a PDL2 binding antagonist. In certain aspects, the PD-1 binding antagonist is a monoclonal antibody or antigen binding fragment thereof. In particular aspects, the PD-1 binding antagonist is nivolumab, pembrolizumab, CT-011, BMS 936559, MPDL328OA or AMP-224. Still in further aspects, an agent is a bifunctional fusion protein targeting PD-L1 and TGFβ, such as M7824 (MSB0011359C).

In certain aspects, the T cell therapy is administered before the anti-platelet agent, simultaneous with the anti-platelet agent, or after the anti-platelet agent. In some aspects, the T cell therapy and anti-platelet agent are administered simultaneously. In certain aspects, the T cell therapy and anti-platelet agent are administered intravenously, intraperitoneally, intratracheally, intratumorally, intramuscularly, endoscopically, intralesionally, percutaneously, subcutaneously, regionally, or by direct injection or perfusion.

In some aspects, the cancer is bladder cancer, breast cancer, clear cell kidney cancer, head/neck squamous cell carcinoma, lung squamous cell carcinoma, melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL). In particular aspects, the cancer is breast cancer. In other aspects, the cancer is melanoma.

In certain aspects, the number of regulatory T cells (Tregs) is decreased in the subject relative to prior to administration of the therapy. In particular aspects, the Tregs are Foxp3$^|$ Tregs.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figures 1A, 1B:
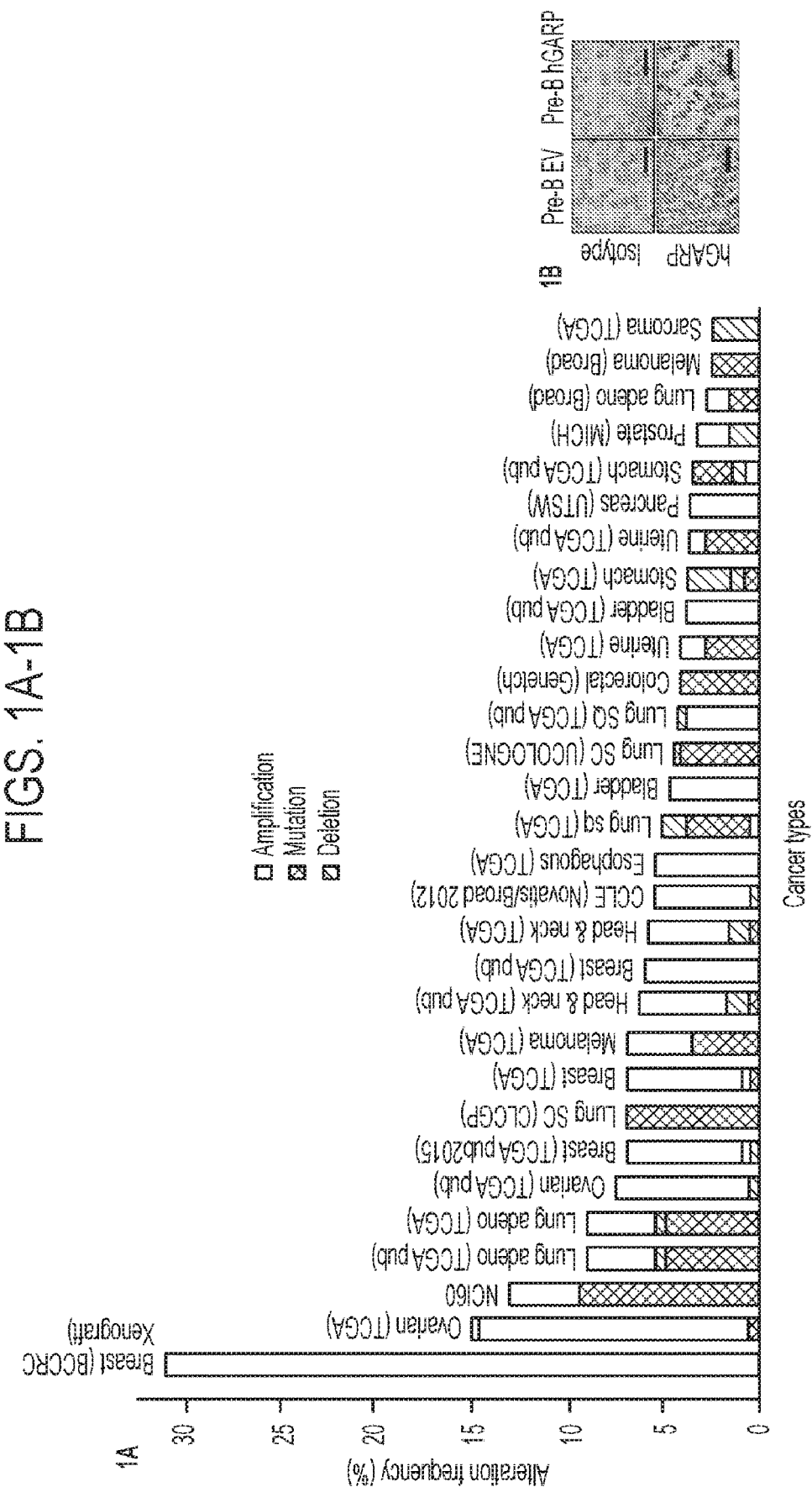
FIGS. 1A-1F. GARP upregulation in cancer correlates with poor prognostic significance. (1A) Summary of cross-cancer alteration studies for GARP. Data were obtained from www.cbioportal.org in response to query for GARP gene LRRC32 on Nov. 16, 2015. (1B) Specificity analysis of hGARP antibody in pre-B EV and pre-B leukemic cells expressing hGARP. (1C) Patient-matched uninvolved and primary breast cancer. Shown are representative images and the IHC GARP scores. (1D) Representative images of GARP IHC (darkened regions) of normal tissues and cancers. Scale bar: 20 µm. (1E) Expression intensity of GARP-positive cells, (1F) Correlation between GARP expression and overall survival of colon and lung cancer (left and middle panel) as well as Gleason score of prostate cancer (right panel). The number of samples (n) are indicated. Kaplan Meier curves are shown in Panel F for lung and colon cancer with p-values calculated by log-rank tests. Two sample t-tests were used to compare group differences in FIGS. 1C, 1E and the prostate cancer in 1F. HR stands for hazard ratio. $*P<0.05$. $P<0.01$. $*P<0.001$. $****P<0.0001$.

It is demonstrated herein that both membrane-bound and soluble GARP is widely expressed by human cancer cells but less by normal epithelial cells, and the expression of GARP correlates uniformly with an advanced stage of cancer and poor prognosis. Additionally, it was found that GARP itself has a transformation potential, which renders normal mammary gland epithelial cells tumorgenic. It was observed that GARP expression in cancer cells led to increased TGF-β activity, likely due to its ability to concentrate LTGF-β in cis as well as trans, to contribute to cancer aggressiveness and metastasis. GARP expression in the tumor microenvironment promoted the induction of regulatory T cells and thus blunting the function of effector T cells against cancers. However, neutralizing GARP by blockings its ability to bind to TGF-β results in anti-cancer activity even, without chemotherapy. In particular, there are provided here new antibody molecules, the 4d3 and 5c5 antibodies that can effectively bind to and neutralize GARP. Thus, the antibodies of the embodiments can be used in methods for treating cancers and enhancing immune response (e.g., in conjunction with an adoptive T-cell therapy).

While T cell therapy has the potential to treat cancer by recognizing and attacking tumor cells, the tumor microenvironment can evade the immune system through the induction of regulatory T cells which blunt the ability of adoptively transferred effector T cells to control cancer. Accordingly, embodiments of the present invention overcomes challenges associated with current technologies by providing methods for the treatment of cancer comprising the combination of a T cell therapy and an anti-platelet agent. In this method, the anti-platelet agent can potentiate the adoptive T cell therapy of tumors as soluble factors secreted from activated platelets have been shown to suppress T cells. For example, it has been shown that platelet-secreted latent TGFβ and GARP can lead to the resistance of cancer cells to adoptive T cell therapy. Thus, anti-platelet factors such as an anti-GARP monoclonal antibody (that can block TGFβ binding) can be used in combination with the T cell therapy to overcome this resistance and treat cancer. In addition, other immunotherapies such as an immune checkpoint inhibitor can be used in combination with the T cell therapy and anti-platelet agent to enhance the immune response.

I. Definitions

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the GARP signaling. In another example, a treatment may include administration of a T cell therapy and a pharmaceutically effective amount of an anti-platelet agent (e.g., an antibody that inhibits the GARP signaling).

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

The term "immune checkpoint" refers to a molecule such as a protein in the immune system which provides inhibitory signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489).

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

II. Antibodies of the Embodiments

In certain embodiments, an antibody or a fragment thereof that binds to at least a portion of GARP protein and inhibits GARP signaling and cancer cell proliferation are contemplated. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-GARP antibody is a monoclonal antibody or a humanized antibody.

Thus, by known means and as described herein, polyclonal or monoclonal antibodies, antibody fragments, and binding domains and CDRs (including engineered forms of any of the foregoing) may be created that are specific to GARP protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a GARP extracellular domain (ECD) protein, in order to produce antibodies specific for GARP protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a GARP antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells ($CD45^+CD5^-CD19^+$) may be isolated from freshly prepared rabbit peripheral blood mononuclear cells of immunized rabbits and further selected for GARP binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into E. coli. GARP specific binding Fab may be selected out through multiple rounds enrichment panning and sequenced. Selected GARP binding hits may be expressed as full-length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881, 557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in: Marks (1992); Stemmer (1994); Gram et al. (1992); Barbas et al. (1994); and Schier et al. (1996).

It is fully expected that antibodies to GARP will have the ability to neutralize or counteract the effects of GARP regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds GARP.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against GARP, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

II. T Cell Therapy

Certain embodiments of the present disclosure concern obtaining and administering T cells to a subject as an immunotherapy to target cancer cells. Several basic approaches for the derivation, activation and expansion of functional anti-tumor effector T cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods of the present disclosure.

A. T Cell Preparation

In some embodiments, the T cells are derived from the blood, bone marrow, lymph, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T ($T_N$) cells, effector T cells ($T_{EFF}$), memory T cells and sub-types thereof, such as stem cell memory T (TSC$_M$), central memory T (TC$_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells). In one embodiment, the cells (e.g., CD8$^+$ cells or CD3$^+$ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Ra (CD127). In some examples, CD8$^+$ T cells are enriched for cells positive for CD45RO (or negative for CD45RA) and for CD62L.

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^|$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining $T_{CM-}$ enriched CD8$^|$ T cells and CD4| T cells further enhances efficacy.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about 2×10$^6$ lymphocytes), e.g., from about 5 to about 21 days, preferably from about 10 to about 14 days. For example, the cells may be cultured from 5 days, 5.5 days, or 5.8 days to 21 days, 21.5 days, or 21.8 days, such as from 10 days, 10.5 days, or 10.8 days to 14 days, 14.5 days, or 14.8 days.

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days, preferably about 14 days. More preferably, rapid expansion provides an increase of at least about 200-fold (e.g., 200-, 300-, 400-, 500-, 600-, 700-, 800-, 900-, or greater) over a period of about 10 to about 14 days, preferably about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

The autologous T-cells can be modified to express a T-cell growth factor that promotes the growth and activation of the autologous T-cells. Suitable T-cell growth factors include, for example, interleukin (IL)-2, IL-7, IL-15, and IL-12. Suitable methods of modification are known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. In particular aspects, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

B. Genetically Engineered Antigen Receptors

The T cell can genetically engineered to express antigen receptors such as engineered TCRs and/or chimeric antigen receptors (CARs). For example, the autologous T-cells are modified to express a T cell receptor (TCR) having antigenic specificity for a cancer antigen. Suitable TCRs include, for example, those with antigenic specificity for a melanoma antigen, e.g., gp100 or MART-1. Suitable methods of modification are known in the art. See, for instance, Sambrook and Ausubel, supra. For example, the T cells may be transduced to express a T cell receptor (TCR) having antigenic specificity for a cancer antigen using transduction techniques described in Heemskerk et al. *Hum Gene Ther.* 19:496-510 (2008) and Johnson et al. *Blood* 114:535-46 (2009).

In some embodiments, the T cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the genetically engineered antigen receptors include a CAR as described in U.S. Pat. No. 7,446,190, and those described in International Patent Application Publication No.: WO/2014055668 A1.

In some aspects, the tumor antigen is a human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1). For example, the target antigen is hTERT or survivin. In some aspects, the target antigen is CD38. In other aspects, the target antigen is CD33 or TIM-3. In other aspects, it is CD26, CD30, CD53, CD92, CD148, CD150, CD200, CD261, CD262, or CD362. In some embodiments, the engineered immune cells can contain an antigen that targets one or more other antigens. In some embodiments, the one or more other antigens is a tumor antigen or cancer marker. Other antigens include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp1OO, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD 123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

1. Chimeric Antigen Receptors

In some embodiments, the engineered antigen receptors include chimeric antigen receptors (CARs), including activating or stimulatory CARs, costimulatory CARs (see WO2014/055668), and/or inhibitory CARs (iCARs, see Fedorov et al., Sci. Transl. Medicine, 5(215) (December, 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

The CAR generally includes at least one intracellular signaling component or components. In some embodiments, the CAR includes an intracellular component of the TCR complex, such as a TCR CD3+ chain that mediates T-cell activation and cytotoxicity, e.g., CD3 zeta chain. Thus, in some aspects, the antigen binding molecule is linked to one or more cell signaling modules. In some embodiments, cell signaling modules include CD3 transmembrane domain, CD3 intracellular signaling domains, and/or other CD transmembrane domains. In some embodiments, the CAR further includes a portion of one or more additional molecules such as Fc receptor γ, CD8, CD4, CD25, or CD16. For example, in some aspects, the CAR includes a chimeric molecule between CD3-zeta (CD3-Q or Fc receptor γ and CD8, CD4, CD25 or CD16.

2. T Cell Receptor (TCR)

In some embodiments, the genetically engineered antigen receptors include recombinant T cell receptors (TCRs) and/or TCRs cloned from naturally occurring T cells. A "T cell receptor" or "TCR" refers to a molecule that contains a variable α and β chains (also known as TCRα and TCRp, respectively) or a variable γ and δ chains (also known as TCRy and TCR5, respectively) and that is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, Immunobiology: The Immune System in Health and Disease, 3 rd Ed., Current Biology Publications, p. 4:33, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., Pwc. Nat'lAcad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., a-chain, β-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., a-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. [0140] In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, a high-affinity T cell clone can be isolated from a patient, and the TCR isolated. In some embodiments, the T-cells can be a cultured T-cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15: 169-180 and Cohen et al. (2005) J Immunol. 175:5799-5808. In some embodiments, phage display is used to isolate TCRs against a target antigen (see, e.g., Varela-Rohena et al. (2008) Nat Med. 14: 1390-1395 and Li (2005) Nat Biotechnol. 23:349-354. In some embodiments, the TCR or antigen-binding portion thereof can be synthetically generated from knowledge of the sequence of the TCR.

III. Methods of Treatment

Certain aspects of the present embodiments can be used to prevent or treat a disease or disorder associated with GARP signaling. Signaling of GARP may be reduced by any suitable drugs to prevent cancer cell proliferation. Preferably, such substances would be an anti-GARP antibody.

Provided herein, in certain embodiments, are methods for treating or delaying progression of cancer in an individual comprising administering to the individual an effective amount an anti-platelet agent and T cell therapy. Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, preneoplastic lesions in the lung, colon cancer, melanoma, and bladder cancer.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

In some embodiments of the methods of the present disclosure, activated CD4 and/or CD8 T cells in the individual are characterized by γ-IFN producing CD4 and/or CD8 T cells and/or enhanced cytolytic activity relative to prior to the administration of the combination. γ-IFN may be measured by any means known in the art, including, e.g., intracellular cytokine staining (ICS) involving cell fixation, permeabilization, and staining with an antibody against γ-IFN. Cytolytic activity may be measured by any means known in the art, e.g., using a cell killing assay with mixed effector and target cells.

A T cell therapy may be administered before, during, after, or in various combinations relative to an anti-platelet agent. The administrations may be in intervals ranging from concurrently to minutes to days to weeks. In embodiments where the T cell therapy is provided to a patient separately from an anti-platelet agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In some embodiments, the subject can be administered nonmyeloablative lymphodepleting chemotherapy prior to the T cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m² fludarabine is administered for five days.

In certain embodiments, a T-cell growth factor that promotes the growth and activation of the autologous T cells is administered to the subject either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

The T cell therapy and anti-platelet agent may be administered by the same route of administration or by different routes of administration. In some embodiments, the T cell therapy and/or anti-platelet agent is administered intravenously, intramuscularly, subcutaneously, topically, orally, transdermally, intraperitoneally, intraorbitally, by implantation, by inhalation, intrathecally, intraventricularly, or intranasally. An effective amount of the T cell therapy and anti-platelet agent may be administered for prevention or treatment of disease. The appropriate dosage of the T cell therapy and anti-platelet agent be determined based on the type of disease to be treated, severity and course of the disease, the clinical condition of the individual, the individual's clinical history and response to the treatment, and the discretion of the attending physician.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (in particular 10 ml), while for tumors of <4 cm, a volume of about 1-3 ml will be used (in particular 3 ml). Multiple injections delivered as single dose comprise about 0.1 to about 0.5 ml volumes.

A. Pharmaceutical Compositions

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

Also provided herein are pharmaceutical compositions and formulations comprising T cell therapy, an anti-platelet agent and a pharmaceutically acceptable carrier.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Anti-Platelet Agents

Embodiments of the present methods concern anti-platelet agents. The phrase "anti-platelet agent" refers to any compound which inhibits activation, aggregation, and/or adhesion of platelets, and is intended to include all pharmaceutically acceptable salts, prodrugs e.g., esters and solvate forms, including hydrates, of compounds which have the activity, compounds having one or more chiral centers may occur as racemates, racemic mixtures and as individual diastereomers or enantiomers with all such isomeric forms and mixtures thereof being included, any crystalline polymorphs, co-crystals and the amorphous form are intended to be included.

Non-limiting examples of antiplatelet agents that may be used in the oral dosage forms of the present invention include adenosine diphosphate (ADP) antagonists or $P_2Yi_2$ antagonists, phosphodiesterase (PDE) inhibitors, adenosine reuptake inhibitors, Vitamin K antagonists, heparin, heparin analogs, direct thrombin inhibitors, glycoprotein IIB/IIIA inhibitors, anti-clotting enzymes, as well as pharmaceutically acceptable salts, isomers, enantiomers, polymorphic crystal forms including the amorphous form, solvates, hydrates, co-crystals, complexes, active metabolites, active derivatives and modifications, pro-drugs thereof, and the like.

ADP antagonists or $P_2Y_{12}$ antagonists block the ADP receptor on platelet cell membranes. This $P_2Yi_2$ receptor is important in platelet aggregation, the cross-linking of platelets by fibrin. The blockade of this receptor inhibits platelet aggregation by blocking activation of the glycoprotein IIb/IIIa pathway. In an exemplary embodiment, the antiplatelet agent is an ADP antagonist or $P_2Yi_2$ antagonist. In another exemplary embodiment, the antiplatelet agent is a thienopyridine. In another exemplary embodiment, the ADP antagonist or $P_2Yi_2$ antagonist is a thienopyridine.

In another exemplary embodiment, the ADP antagonist or $P_2Yi_2$ antagonist is a member selected from sulfinpyrazone, ticlopidine, clopidogrel, prasugrel, R-99224 (an active metabolite of prasugrel, supplied by Sankyo), R-1381727, R-125690 (Lilly), C-1330-7, C-50547 (Millennium Pharmaceuticals), INS-48821, INS-48824, INS-446056, INS-46060, INS-49162, INS-49266, INS-50589 (Inspire Pharmaceuticals) and Sch-572423 (Schering Plough). In another exemplary embodiment, the ADP antagonist or $P_2Yi_2$ antagonist is ticlopidine hydrochloride (TICLID™). In another exemplary embodiment, the ADP antagonist or $P_2Yi_2$ antagonist is a member selected from sulfinpyrazone, ticlopidine, AZD6140, clopidogrel, prasugrel and mixtures thereof. In another exemplary embodiment, the ADP antagonist or $P_2Yi_2$ antagonist is clopidogrel. In another exemplary embodiment, the therapeutically effective amount of clopidogrel is from about 50 mg to about 100 mg. In another exemplary embodiment, the therapeutically effective amount of clopidogrel is from about 65 mg to about 80 mg. In another exemplary embodiment, the ADP antagonist or $P_2Yi_2$ antagonist is a member selected from clopidogrel bisulfate (PLA VIX™), clopidogrel hydrogen sulphate, clopidogrel hydrobromide, clopidogrel mesylate, cangrelor tetrasodium (AR-09931 MX), ARL67085, AR-C66096 AR-C 126532, and AZD-6140 (AstraZeneca). In another exemplary embodiment, the ADP antagonist or $P_2Yi_2$ antagonist is prasugrel. In another exemplary embodiment, the therapeutically effective amount of prasugrel is from about 1 mg to about 20 mg. In another exemplary embodiment, the therapeutically effective amount of clopidogrel is from about 4 mg to about 11 mg. In another exemplary embodiment, the ADP antagonist or $P_2Yi_2$ antagonist is a member selected from clopidogrel, ticlopidine, sulfinpyrazone, AZD6140, prasugrel and mixtures thereof.

In certain embodiments the anti-platelet agent is clopidogrel or a pharmaceutically acceptable salt, solvate, polymorph, co-crystal, hydrate, enantiomer or prodrug thereof. In another embodiment clopidogrel or pharmaceutically acceptable salt, solvate, polymorph, co-crystal, hydrate, enantiomer or prodrug thereof is a powder.

A PDE inhibitor is a drug that blocks one or more of the five subtypes of the enzyme phosphodiesterase (PDE), preventing the inactivation of the intracellular second messengers, cyclic adenosine monophosphate (cAMP) and cyclic guanosine monophosphate (cGMP), by the respective PDE subtype(s). In an exemplary embodiment, the antiplatelet agent is a PDE inhibitor. In an exemplary embodiment, the antiplatelet agent is a selective cAMP PDE inhibitor, hi an exemplary embodiment, the PDE inhibitor is cilostazol (Pletal™).

Adenosine reuptake inhibitors prevent the cellular reuptake of adenosine into platelets, red blood cells and endothelial cells, leading to increased extracellular concentrations of adenosine. These compounds inhibit platelet aggregation and cause vasodilation, hi an exemplary embodiment, the antiplatelet agent is an adenosine reuptake inhibitor. In an exemplary embodiment, the adenosine reuptake inhibitor is dipyridamole (Persantine™).

Vitamin K inhibitors are given to people to stop thrombosis (blood clotting inappropriately in the blood vessels). This is useful in primary and secondary prevention of deep vein thrombosis, pulmonary embolism, myocardial infarctions and strokes in those who are predisposed. In an exemplary embodiment, the anti-platelet agent is a Vitamin K inhibitor, hi an exemplary embodiment, the Vitamin K inhibitor is a member selected from acenocoumarol, clorindione, dicumarol (Dicoumarol), diphenadione, ethyl biscoumacetate, phenprocoumon, phenindione, tioclomarol and warfarin.

Heparin is a biological substance, usually made from pig intestines. It works by activating antithrombin III, which blocks thrombin from clotting blood. In an exemplary embodiment, the antiplatelet agent is heparin or a prodrug of heparin. In an exemplary embodiment, the antiplatelet agent is a heparin analog or a prodrug of a heparin analog. In an exemplary embodiment, the heparin analog a member selected from Antithrombin III, Bemiparin, Dalteparin, Danaparoid, Enoxaparin, Fondaparinux (subcutaneous), Nadroparin, Parnaparin, Reviparin, Sulodexide, and Tinzaparin.

Direct thrombin inhibitors (DTIs) are a class of medication that act as anticoagulants (delaying blood clotting) by directly inhibiting the enzyme thrombin. In an exemplary embodiment, the antiplatelet agent is a DTI. In another exemplary embodiment, the DTI is univalent. In another exemplary embodiment, the DTI is bivalent. In an exemplary embodiment, the DTI is a member selected from hirudin, bivalirudin (IV), lepirudin, desirudin, argatroban (IV), dabigatran, dabigatran etexilate (oral formulation), melagatran, ximelagatran (oral formulation but liver complications) and prodrugs thereof.

In an exemplary embodiment, the anti-platelet agent is a member selected from aloxiprin, beraprost, carbasalate calcium, cloricromen, defibrotide, ditazole, epoprostenol, indobufen, iloprost, picotamide, rivaroxaban (oral FXa inhibitor) treprostinil, triflusal, or prodrugs thereof.

In certain embodiments, the anti-platelet agent is an antibody or a fragment thereof that binds to at least a portion of GARP protein. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-GARP antibody is a monoclonal antibody or a humanized antibody. Thus, by known means and as described herein, polyclonal or monoclonal antibodies, antibody fragments, and binding domains and CDRs (including engineered forms of any of the foregoing) may be created that are specific to GARP protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

C. Additional Therapy

In certain embodiments, the compositions and methods of the present embodiments involve an antibody or an antibody fragment against GARP to inhibit its activity in cancer cell proliferation, in combination with a second or additional therapy. Such therapy can be applied in the treatment of any disease that is associated with GARP-mediated cell proliferation. For example, the disease may be cancer.

In certain embodiments, the compositions and methods of the present embodiments involve a T cell therapy and an anti-platelet agent in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

The methods and compositions, including combination therapies, enhance the therapeutic or protective effect, and/ or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

Various combinations may be employed. For the example below an antibody therapy, or a T cell therapy and anti-platelet agent, is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaII); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen (Carter et al., 2008; Teicher 2014; Leal et al., 2014). Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach (Teicher 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., Mycobacterium bovis, Plasmodium falciparum, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, Nat Rev Cancer, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyteassociated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) Proc Natl Acad Sci USA 95(17): 10067-10071; Camacho et al. (2004) J Clin Oncology 22(145): Abstract No. 2505 (antibody CP-675206); and Mokyr et al. (1998) Cancer Res 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. Articles of Manufacture or Kits

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, at least one GARP antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

In some embodiment, an article of manufacture or a kit is provided comprising adoptive T cells and an anti-platelet agent (e.g., anti-GARP antibody) is also provided herein. The article of manufacture or kit can further comprise a package insert comprising instructions for using the adoptive T cells in conjunction with an anti-platelet agent to treat or delay progression of cancer in an individual or to enhance immune function of an individual having cancer. Any of the adoptive T cells and/or anti-platelet agents described herein may be included in the article of manufacture or kits. In some embodiments, the adoptive T cells and anti-platelet agent are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Expression of GARP in Cancer Cells

Figure 1C:
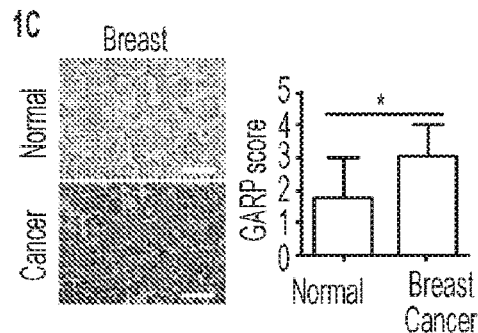
Figure 1D:
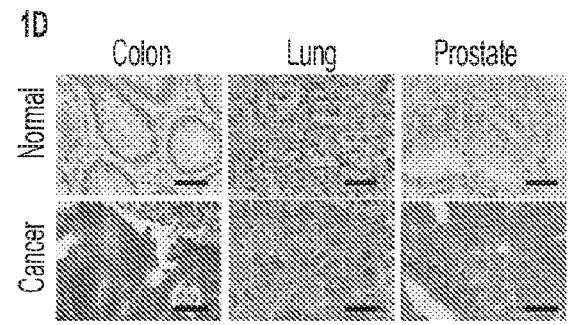
Figure 1E:
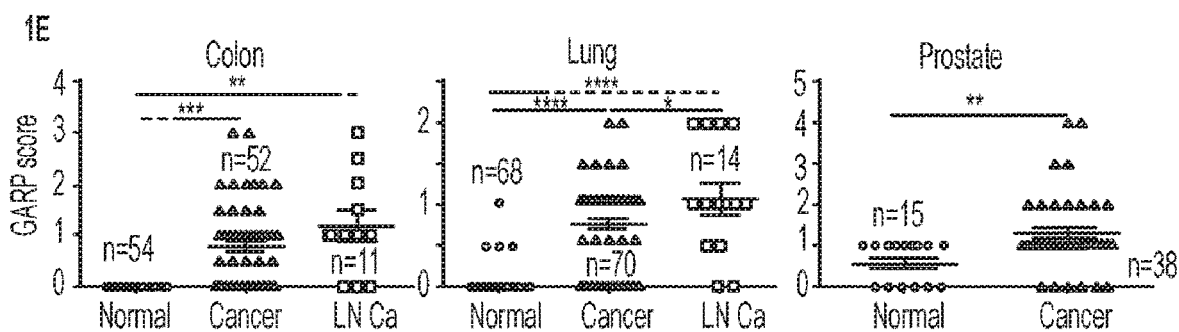
Figure 1F:
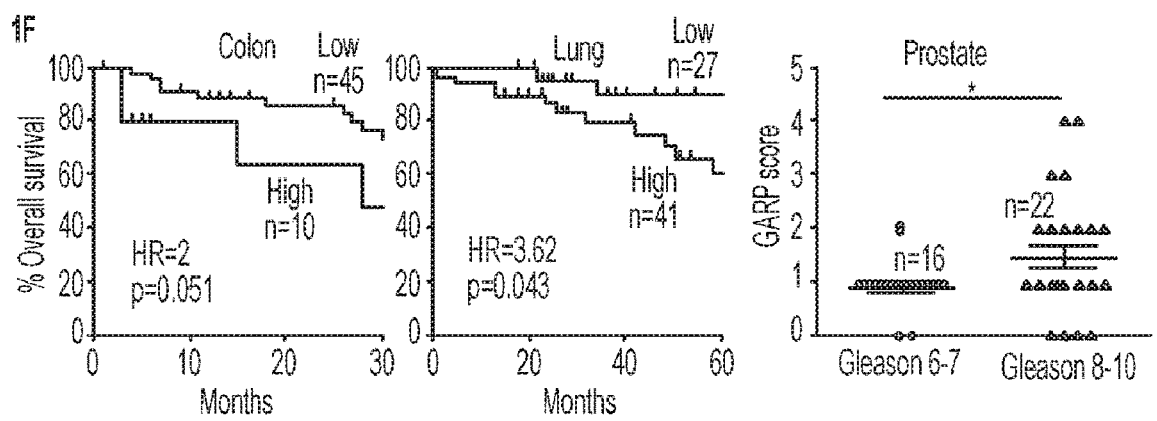

Recent studies, including The Cancer Genome Atlas (TCGA) project, have shown that LRRC32 is amplified in up to 30% of patients with many human cancer types, including ovarian, lung, breast, and head and neck cancers (FIG. 1A). To examine GARP protein expression, immunohistochemistry (IHC) was performed on a human tumor microarray from archived human tumors and it was subsequently determined whether GARP expression carried any prognostic significance. The specificity of the anti-human GARP antibody was ascertained by its staining of a Pre-B leukemia cell line stably transfected with human GARP (FIG. 1B). Given that LRRC32 was amplified in human breast cancer (Szepetowski et al., 1992), GARP expression was first evaluated in breast cancer patients using IHC. The results were read and scored by a clinical pathologist in a double-blinded fashion. IHC analysis of patient-matched uninvolved breast tissue versus primary breast cancer (n=16) indicated a significant increase of GARP expression on cancer tissues in 9 out of 16 patients (FIG. 1C). By RT-PCR, GARP mRNA expression was increased by ≥2-fold in 28.5% of patients with breast cancer (n=42) compared with normal breast tissues. IHC was then performed on cancer specimens, including 55 colon cancer specimens, 55 adjacent normal tissues, and 11 corresponding lymph nodes, and adjacent normal tissues (FIG. 1D). Normal epithelial specimens showed no significant GARP positivity (FIGS. 1D and 1E). However, the primary cancers (colon and lung) and lymph node (LN) metastatic tissues stained variably positive for GARP (uniformly negative with isotype control antibody) (FIG. 1E). Compared to the undetectable level (defined as 0) in normal tissue, the percentage of GARP positive cells was 26.1% ($p=8.6\times10^{-9}$) in primary cancer and 25% (p=0.008) in LN metastasis. On a scale of 0 to 4, GARP intensity score ranged between 0 and 3, averaging at 0.78 ($p=1.1\times10^{-8}$) in primary colon cancers and 1.18 (p=0.003) in LN metastasis (FIG. 1E). Similarly, significantly increased GARP levels were found in primary cancers of the lung and the prostate (FIG. 1E). More importantly, GARP levels correlated inversely with overall survival in patients with colon and lung cancer, regardless of the pathological grade of tumors or lymph node status of the disease (FIG. 1F). High GARP expression also correlated with high Gleason score in prostate cancer (p=0.035) (FIG. 1F). These results demonstrate for the first time that GARP is widely expressed in human cancers, and that the level of expression correlates with disease aggressiveness.

Figures 2A, 2B, 2C, 2D, 2E, 2F:
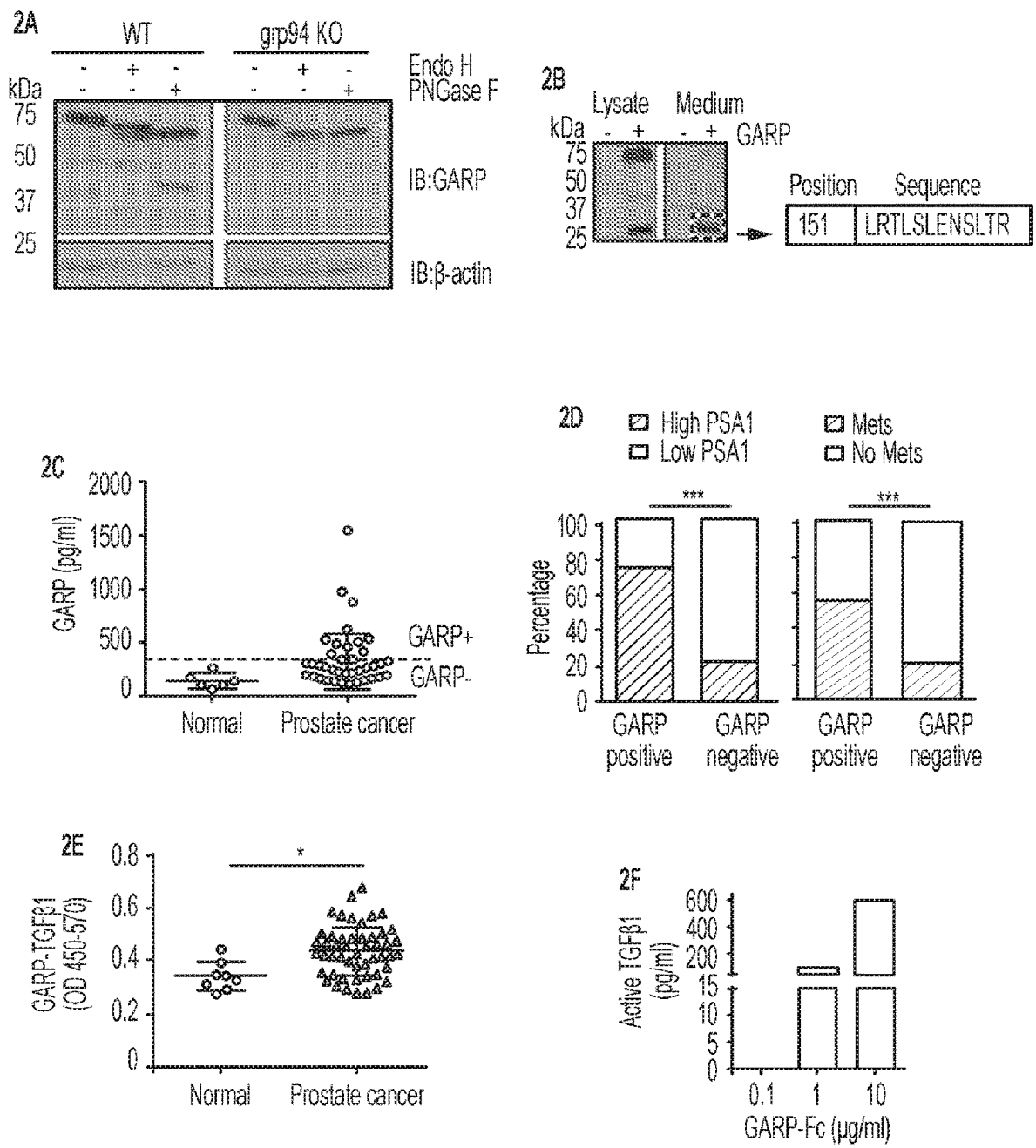
FIGS. 2A-2F. Shedding of membrane-bound GARP from cancer cells and its significance as a potential cancer biomarker. (2A) GARP cleavage in the post-ER compartment occurs only in the presence of grp94. N-terminal FLAG-tagged GARP was stably expressed in WT or grp94 Pre-B KO cells. The whole cell lysate was treated with Endo H or PNGase F followed by immunoblot with FLAG antibody. (2B) Lower fragment protein is GARP based on both immunoreactivity and mass spectrometry analysis. The peptide sequence from GARP that was identified by mass spectrometry is indicated (SEQ ID NO: 17). (2C) Soluble GARP in the serum of prostate cancer patients and control normal subjects. (2D) Correlation analysis between GARP positivity and PSA1 level (left panel), the GARP positivity and the metastatic status of prostate cancer (right panel). (2E) Quantification of GARP-TGF-β1 complex in the sera of prostate cancer patients and normal subjects by a sandwich ELISA. (2F) Active TGFβ ELISA level from purified recombinant soluble GARP-Fc. The difference in distribution in FIG. 2D was calculated by Chi-squared test. Two sample t-tests were used to compare group differences in FIG. 2E. $*p<0.05$. $***P<0.001$.

In vitro biochemical studies have established that GARP also exists in a soluble form that is secreted in complex with latent TGF-β1 from Treg cells (Gauthy et al., 2013). It has also been shown that GARP depends on the molecular chaperone grp94 in the endoplasmic reticulum for folding and cell surface expression (Zhang et al., 2015). To determine whether GARP secretion is a Treg cell-specific event or a GARP-intrinsic phenomenon, N-terminal hemagglutinin (HA)-tagged GARP was expressed in murine Pre-B cells with and without grp94, and then GARP expression was analyzed in cell lysates and conditioned media. Three GARP bands were observed only in gp96+ (WT) cells: approximately 75, 45, and 30 kDa in molecular weight, respectively (FIG. 2A). The 45 and 30 kDa fragments appeared to be the postranslationally cleaved products of the full-length cell surface GARP (75 kDa) because they were more resistant to Endo H compared with PNGase F and were found in WT, but not grp94 KO cells. If so, the 30 kDa N-terminal GARP fragment should be liberated from the cell surface into the media. Indeed, gel extraction and sequencing of the 30 kDa protein in the media by mass spectrometry confirmed that it was derived from the N-terminal fragment of GARP (FIG. 2B).

It was next determined whether soluble GARP (sGARP) was present in the sera of cancer patients and whether the serum levels of sGARP had any prognostic significance. Sera were collected from male normal controls (n=7) and prostate cancer patients (n=48) and analyzed for GARP by ELISA. It was found that sGARP was present in serum from both normal individuals and from prostate cancer patients (FIG. 2C). Further analysis revealed that higher GARP levels correlated with increased prostate cancer specific antigen (PSA) levels and metastasis (FIG. 2D). Moreover, the presence of the sGARP-TGF-β1 complex was evaluated in the serum of prostate cancer patients and normal controls using a GARP-TGF-β1 sandwich ELISA. As predicted, cancer patients' sera contained higher levels of soluble GARP and TGF-β1 complex than normal subjects (FIG. 2E). To gain insight into the function of soluble GARP, a fusion protein was prepared consisting of the N-terminal extracellular domain of GARP linked to an Fc domain of IgG (GARP-Fc). The construct was expressed in the Chinese hamster ovary (CHO) cells. The GARP fusion protein was then purified from the conditioned medium. As measured by active TGF-β ELISA, a direct association was found between GARP-Fc and active TGF-β1 (FIG. 2F), indicating the presence of GARP-Fc-TGF-β1 complexes. This finding is in agreement with the previously reported immunosuppressive nature of sGARP (Hahn et al., 2013).

Example 2

GARP and TGF-β

Figures 3A, 3B, 3C, 3D, 3E, 3F, 3G, 3H:
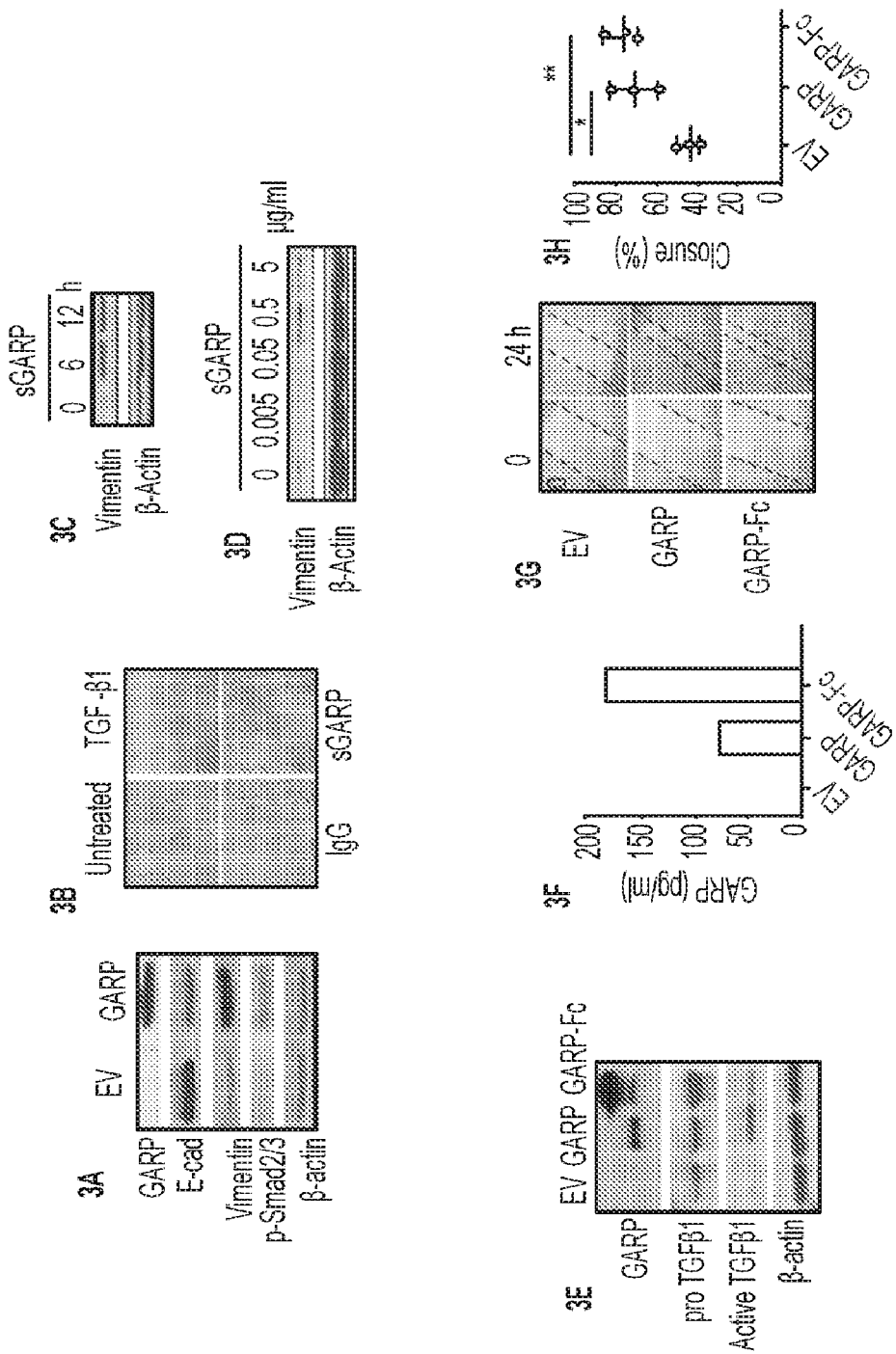
FIGS. 3A-3J. Enforced GARP expression on normal mammary gland epithelial cells enhances TGF-β signaling and drives epithelial-mesenchymal cell transition (EMT) and invasion. (3A) NMuMG cells were transfected to stably express membrane bound GARP, followed by Western blot for E-cadherin, vimentin and phosphor-SMAD-2/3. (3B) NMuMG cells were treated with the recombinant human TGF-β1 soluble GARP, and isotype antibody control or left untreated in serum-free medium for 24 h, followed by morphological analysis. (3C) NMuMG cells were treated for the indicated time with soluble GARP-Fc (sGARP) in serum-free medium. Vimentin upregulation was detected by Western blot analysis. (3D) NMuMG cells were treated with increasing doses of soluble GARP, followed by immunoblot for vimentin. (3E) Immunoblot of GARP, TGFβ and β-actin control. (3F) ELISA quantification of soluble GARP in the condition medium of NMuMG EV, GARP, and GARP-Fc cells. (3G) In vitro scratch assay to indicate the difference in the gap closure at 24 h. (3H) Summary of three independent scratch assays. (3I) In vivo imaging of the luciferin-enhanced bioluminescence in mice after injection of GARP, GARP-Fc and control NMuMG cells at week 3 and 6. (3J) Histological analysis of NMuMG-GARP tumors by H&E, and expression of vimentin and E-cadherin by IHC. Scale bar: 20 µm. Two sample t-tests were used to compare group differences in FIG. 3H. $*P<0.05$. $**P<0.01$. Two independent experiments were performed with similar findings.
Figures 3I, 3J:
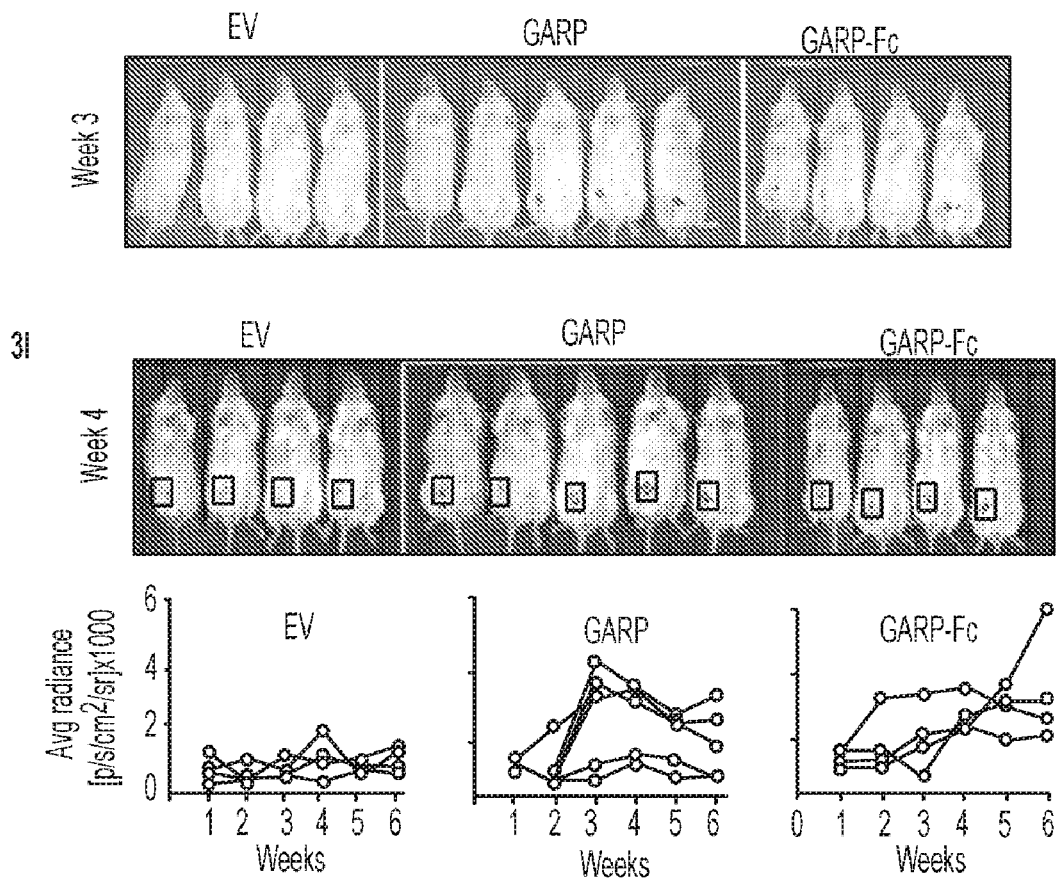

Enforced GARP expression in normal murine mammary epithelial cells upregulates TGF-β expression and drives oncogenesis. In normal murine mammary gland epithelia (NMuMG) cells, TGF-β exerts both a growth inhibitory response and an epithelial-to-mesenchymal cell transition (EMT) response (Xie et al., 2003). As such, NMuMG cells have been extensively utilized to study TGF-β signaling and biology (Xu et al., 2009). Given that GARP regulates the bioavailability of TGF-β, NMuMG cells were used in a bioassay to study the effect of both membrane-bound GARP and soluble GARP on epithelial cells. It was found that stable GARP expression induced Smad-2/3 phosphorylation and expression of vimentin, but downregulated E-cadherin, consistent with increased canonical TGF-β signaling (FIG. 3A). Moreover, NMuMG cells stimulated with soluble GARP-Fc changed from their typical polygonal and flattened epithelial cell morphology to a spindle-shaped morphology within 24 hours (FIG. 3B), with an accompanying time- and dose-dependent upregulation of vimentin (FIGS. 3C and 3D). As expected, NMuMG cells stably expressing either GARP or GARP-Fc had higher expression of active TGF-β1 (FIG. 3E) as well as soluble GARP (FIG. 3F), compared to cells transduced with empty vector (EV). An in vitro "scratch" assay was performed to gauge the migratory properties of GARP-expressing cells. The closure rate of the gap (created by scratching the culture plate) was significantly increased with GARP-expressing cells, indicating increased acquired migratory ability (FIGS. 3G and 3H). It was also examined whether enforced GARP expression enabled NMuMG cells to establish tumors in vivo. To this end, female immunodeficient NOD-Rag1$^{-/-}$ mice were injected in the fourth mammary fat pad with GARP-expressing NMuMG cells or with EV control cells all of which were also engineered to co-express luciferase. By in vivo imaging of the bioluminescence, it was found that the bioactive mass formed only in mice that received GARP$^l$ or GARP-Fc$^l$ NMuMG, but not in mice receiving EV transduced cells (FIG. 3I). The tumor formation by GARP-expressing cells was confirmed by histology (FIG. 3J). Collectively, these results demonstrate that GARP has a transforming property via upregulation of TGF-β, identifying GARP as a potential novel oncogene.

Figure 4A:
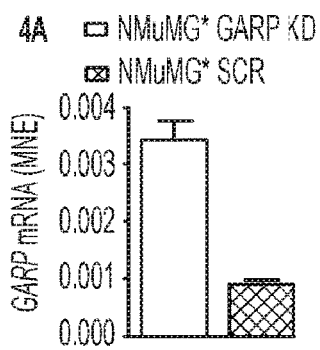
FIGS. 4A-4G. GARP silencing blocks growth and metastasis of mammary carcinoma, (4A) ShRNA knockdown of GARP mRNA in NMuMG* cells. Cells treated with scrambled shRNA (SCR) were used as control. (4B) Flow cytometric analysis of cell surface GARP expression by GARP KD and SCR NMuMG* cells. (4C) Immunoblot of total GARP and TGF-β level in GARP KD and SCR NMuMG cells. (4D) MTT assay to compare the growth kinetics of NMuMG*-SCR with NMuMG*-GARP-KD cells. (4E-4G) NMuMG* SCR and NMuMG*-GARP KD cells were injected into NOD-Rag1$^{-/-}$ mice, followed by monitoring the tumor growth kinetics (4G) and tumor metastasis (4F and 4G). Tumor growth differences in FIGS. 4D and 4E were calculated by 2-way ANOVA. Two sample t-tests were used to compare group differences in FIGS. 4F and 4G. $**P<0.01$.
Figure 4B:
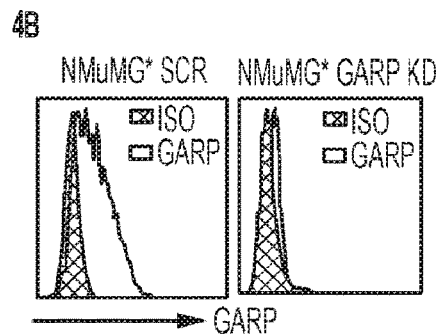
Figure 4C:
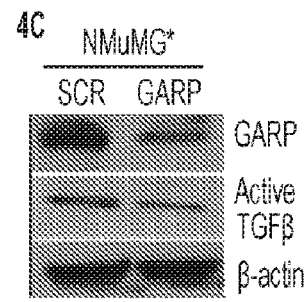
Figure 4D:
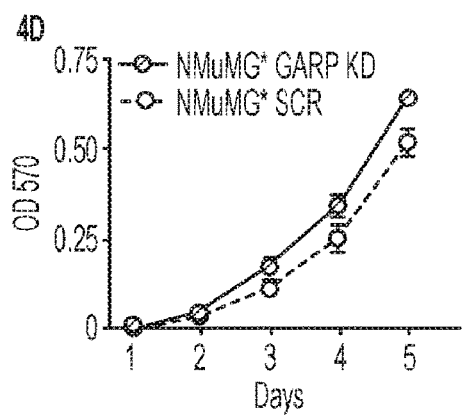
Figure 4E:
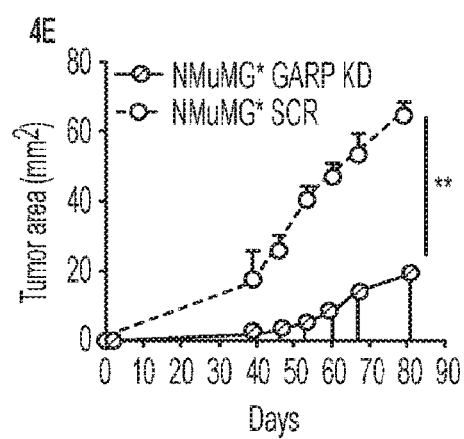
Figure 4F:
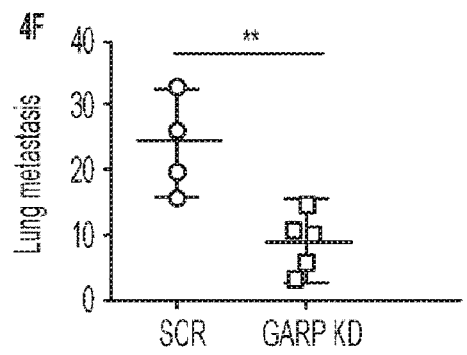
Figure 4G:
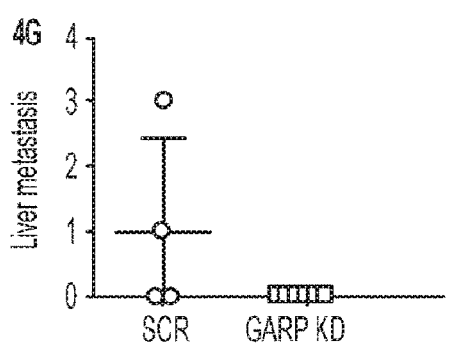

Silencing GARP delays tumor growth. A variant of the normal murine mammary gland epithelial cell line (NMuMG*), in which an RNA-binding protein hnRNPE1 is knocked down by RNA interference, was recently described as being capable of forming tumors in nude mice (Howley et al., 2015). Intriguingly, it was found that these cells expressed a significant level of endogenous GARP (FIGS. 4A-4C), raising the possibility that heightened TGF-β biogenesis, in addition to the silencing of the TGF-β-mediated translation repression complex, drives mammary cancer in this model. To test this hypothesis, short hairpin RNA (shRNA) knock down (KD) of GARP was performed in the NMuMG* cells (FIGS. 4A-4C). GARP silencing did not affect the in vitro proliferation of NMuMG* cells as determined by MTT assay (FIG. 4D). Remarkably, silencing of GARP alone in the NMuMG* cells significantly attenuated their growth in vivo (FIG. 4E). Further, the ability of these GARP KD cells to metastasize to the lungs and liver was compromised (FIGS. 4F and 4G).

Figure 5A:
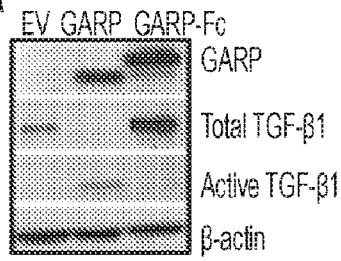
FIGS. 5A-5J. GARP upregulation in murine mammary cancer cells promotes TGF-β activation, tumor growth, metastasis and immune tolerance. (5A) Immunoblot for GARP, TGF-β and β-actin control in 4T1 cells stably engineered to express GARP, GARP-Fc or control EV. (5B) Quantification of active TGF-β1 by ELISA in the 72 h conditioned medium from 4T1 EV, GARP and GARP-Fc cells. (5C) Naïve CD4$^+$ T cells were stimulated with anti-CD3, and anti CD-28 mAb in the presence of 50% 3-day condition medium from 4T1-EV, 4T1-GARP and 4T1-GARP-Fc cells. Foxp3 expression was analyzed on day 3 by flow cytometry. (5D) Female BALB/c mice were injected in the 4$^{th}$ mammary fat pad of indicated tumors. Tumors volume was measured every 3 days. (5E) The weight of tumors in grams at the end point of (5D). (5F) Lungs were isolated and paraffin-embedded. Numbers of tumor nodules in the lungs were counted. (5G) The 3-week tumors were isolated and embedded in OCT. Fresh frozen sections were stained for p-SMAD-2/3 mAb. Scale bar: 100 µm. (5H) Summary statistics for p-SMAD-2/3 staining intensity, defined independently by the studying pathologist. (5I-5J) Tumor-infiltrating lymphocytes were isolated and the numbers of CD4$^+$CD25$^+$Foxp3$^+$ Tregs were enumerated by flow cytometry. (5I) Representative flow plots. (5J) Summary of the percentage of Tregs in the tumor microenvironment. Tumor growth difference in FIG. 5D was calculated by 2-way ANOVA. Two sample t-tests were used to compare group differences in other Panels. $*P<0.05$. $P<0.01$. $*P<0.001$.
Figure 5B:
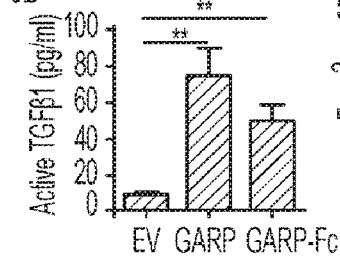
Figure 5C:
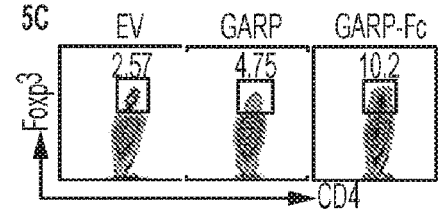
Figure 5D:
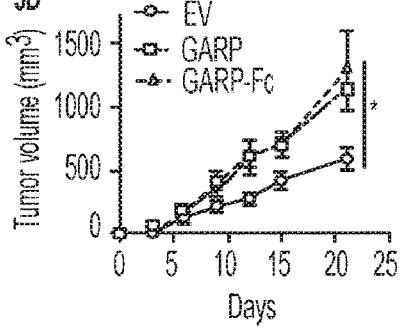
Figure 5E:
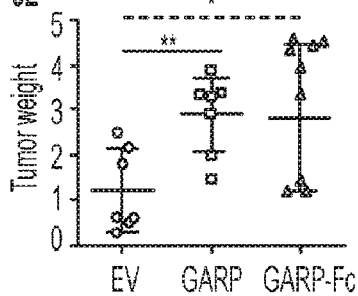
Figure 5F:
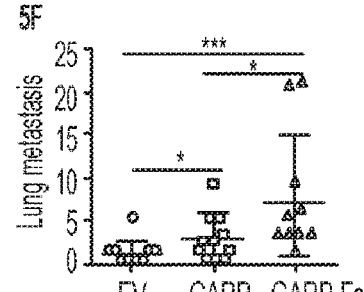
Figure 5G:
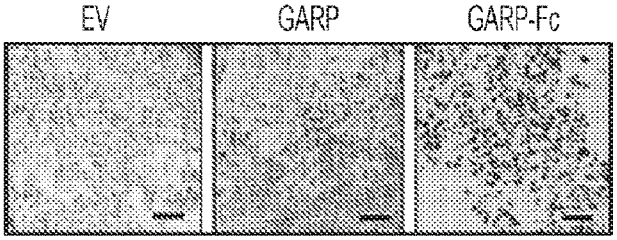
Figure 5H:
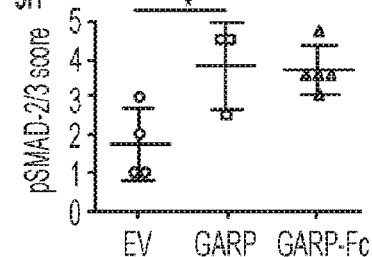
Figure 5I:
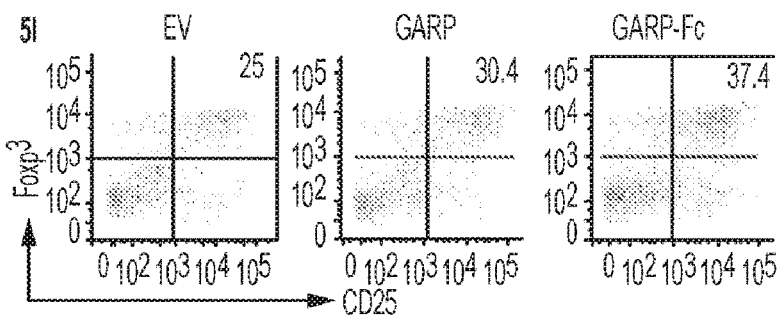
Figure 5J:
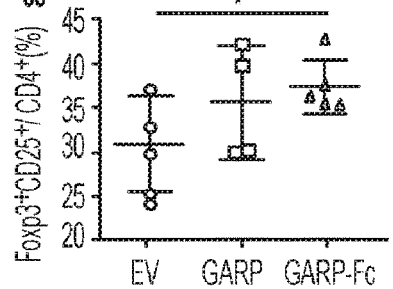

GARP upregulation in murine mammary cancer cells promotes TGF-β activation, tumor growth, metastasis and immune tolerance. LRRC32 was initially described in breast cancer as a frequently amplified gene (Ollendorff et al., 1994), and TGF-β signaling has been shown to promote breast cancer invasion and metastasis (Massague, 2008; Padua et al., 2008; Siegel et al., 2003). However, an understudied aspect of TGF-β biology in cancer is the cancer-extrinsic role of TGF-β via modulating the host immune response (Li and Flavell, 2008). Thus, the impact of GARP on cancer growth and metastasis in a syngeneic immune-sufficient setting was examined in the highly aggressive and metastatic 4T1 mammary carcinoma model in BALB/c mice (Pulaski and Ostrand-Rosenberg, 2001). Similar to the NMuMG system, the over-expression of GARP or GARP-Fc in 4T1 cells led to increased production of active TGF-β (FIGS. 5A and 5B). One of the key mechanisms by which TGF-β inhibits tumor-specific immunity is via the induction of Foxp3$^+$ Tregs. To this end, purified naive CD4$^+$ T cells were cultured in vitro with conditioned media from 4T1-GARP, 4T1-GARP-Fc and empty vector (EV) control cells in the presence of polyclonal T cell activators for 3 days. The conditioned media from GARP-expressing cells was 2-3 fold more efficient at inducing Treg differentiation compared to media from control cells (FIG. 5C). 4T1-EV, 4T1-GARP and 4T1-GARP-Fc cells were injected orthotopically in the fourth right mammary fat pad of 6-8 weeks old female BALB/c mice. It was found that GARP-expressing cells were more aggressive, as indicated by both increased growth kinetics of the primary tumor (FIGS. 5D and 5E) and increased lung metastasis (FIG. 5F). It was also found that this aggressiveness correlated with enhanced TGF-β signaling in the tumor microenvironment as determined by increased p-Smad-2/3 in cancer cells (FIGS. 5G and 5H), as well as by expansion of tolerogenic Treg cells (FIGS. 5I and 5J).

Example 3

Melanoma Studies

Figures 6A, 6B, 6C, 6D, 6E, 6F, 6G:
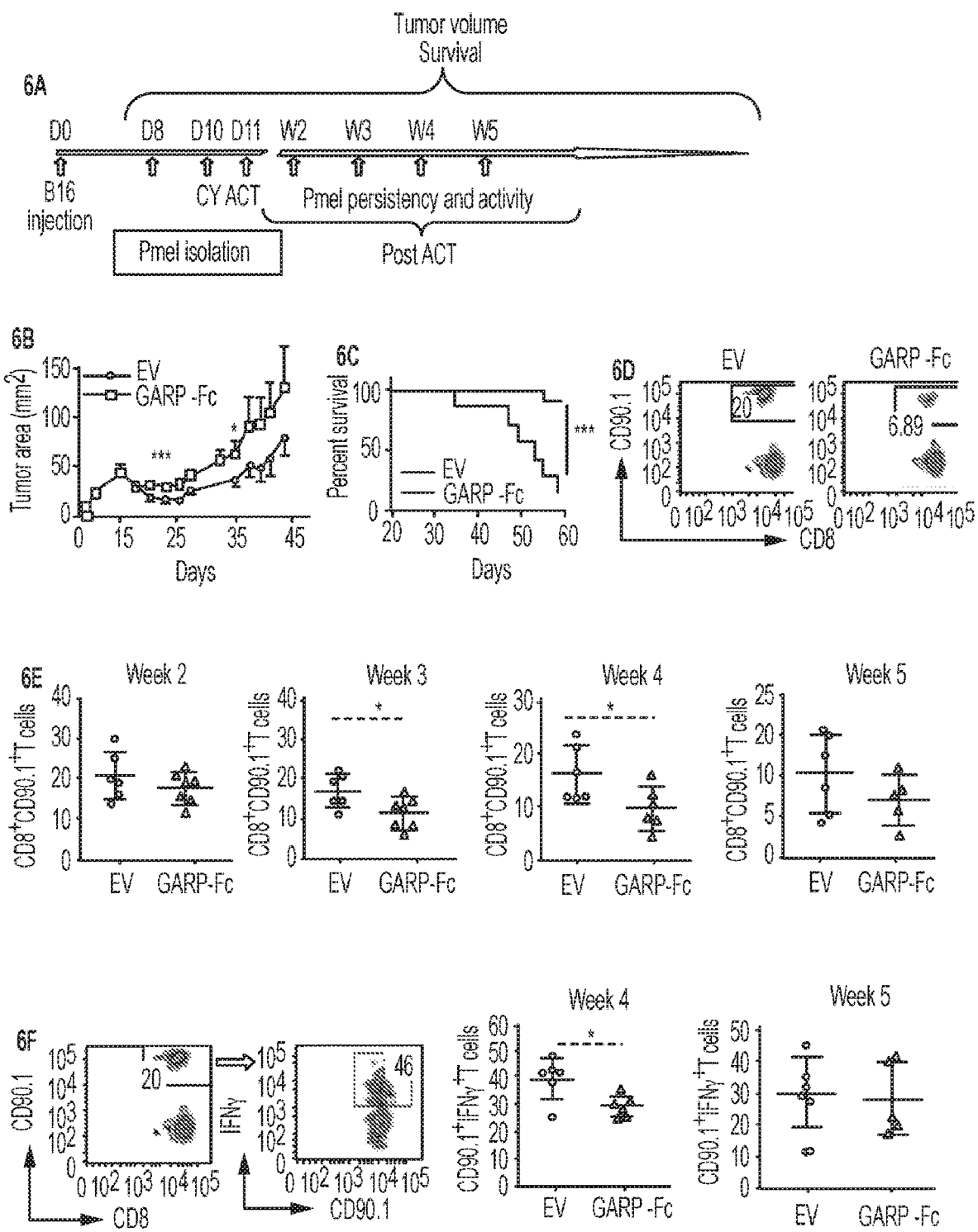
FIGS. 6A-6G. GARP upregulation in B16 mouse melanoma tumor diminishes the effect of the adoptive T cell immunotherapy. (6A) Experimental scheme. (6B) Average tumor growth kinetics of B16-GARP-Fc and B16-EV (n=6). (6C) Difference in survival between two experimental groups as indicated. (6D) A representative FACS plot of antigen-specific donor T cells in the peripheral blood indicated by CD8$^+$CD90.1$^+$ surface marker. (6E) Frequency of donor T cells in the peripheral blood of tumor-bearing mice at different time points post ACT. (6F) A representative FACS plot of intracellular IFNγ stain of peripheral blood antigen-specific donor T cells in response to stimulation by the cognate gp100 peptide. (6G) Quantification of the frequency of IFNγ-producing donor T cells in the peripheral blood of mice received either B16-GARP-Fc or B16-EV. The p-value in FIG. 6C was calculated by log-rank test. Two sample t-tests were used to compare group differences in other panels. *P<0.05. ***P<0.001.

The studies in the 4T1 tumor model prompted the question of whether GARP exerts an inhibitory effect on the function of tumor-specific T cells. To address this possibility, a B16 melanoma model with a defined antigen specificity was utilized along with CD8$^+$ T cell receptor (TCR) transgenic mice (Pmel) with T cells specific for the melanoma-associated antigen gp100 (Muranski et al., 2008; Overwijk et al., 2003). B16-F1 cells were prepared with or without GARP-Fc, and then injected subcutaneously in C57BL/6 mice. The tumor bearing mice were then lymphodepleted with cyclophosphamide (CY) before adoptive cell transfer (ACT) of ex-vivo activated Pmel cells (Rubinstein et al., 2015) (FIG. 6A). It was found that expression of GARP-Fc by B16 cells led to increased resistance to ACT (FIGS. 6B and 6C), which was associated with reduced numbers of antigen-specific Pmel cells in the recipient mice, particularly during the first four weeks of tumor growth when the tumor surface area was less than 100 mm$^2$ (FIGS. 6D and 6E). Similarly, the ability of Pmel CD8$^+$ T cell cells to produce IFNγ in response to antigen stimulation was also impaired in mice bearing GARP-Fc$^+$B16 melanoma (FIGS. 6F and 6G).

Example 4

GARP as a Novel Therapeutic Target in Cancer

Figures 7A, 7B, 7C, 7D, 7E:
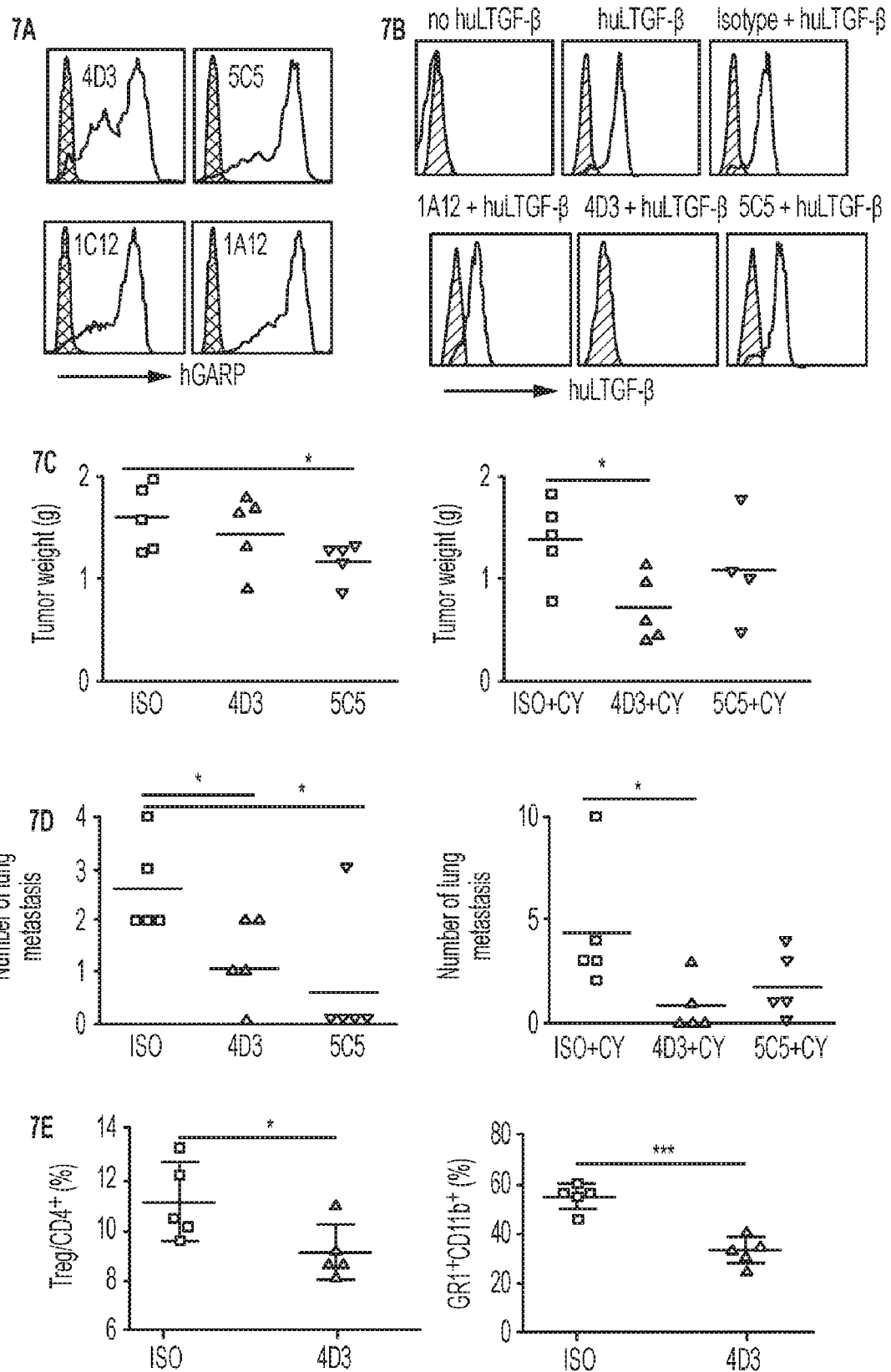
FIGS. 7A-7E. GARP-specific antibodies block binding of exogenous LTGF-β to GARP and have therapeutic values against a preclinical model of breast cancer. (7A) Surface staining of Pre-B cells stably expressing human GARP (Pre-B-hGARP) by various GARP antibodies. Grey histogram represents staining with isotype control antibody. (7B) Pre-B-hGARP cells were incubated without or with human LTGF-β (huLTGF-β), in the presence of various GARP antibodies or Isotype control antibody, followed by staining for cell surface huLTGF-β. (7C) BALB/c mice were injected with 4T1-huGARP mammary tumors orthotopically, followed by indicated treatment regimen. Data shown are the comparisons of primary tumor weight isolated at 35 days (left panel, combined treatment group) or 30 days (right panel, antibody treatment alone) after inoculation. (7D) Impact of anti-GARP antibody treatment alone (left panel) or in combination with CY on the number of metastatic tumor nodules in the lungs. (7E) Percentage of splenic Tregs and MDSCs in the spleen of mice treated with isotype control antibody or anti-GARP antibody (4D3). Two sample t-tests were used to compare group differences in all panels. *P<0.05. ***P<0.001.

The studies described herein have demonstrated that GARP is aberrantly expressed in multiple human cancers, and that GARP expression in murine tumors is associated with increased TGF-β bioavailability, cancer aggressiveness, and T cell tolerance. It was next determined whether GARP could serve as a novel therapeutic target in cancer, using an antibody-based strategy. For the generation of anti-GARP monoclonal antibodies (mAbs), mice were immunized with recombinant human GARP, followed by boosting with irradiated whole myeloma SP2/0 cells stably expressing human GARP, with the aim of generating mAbs against GARP that were conformation-specific. More than 20 mAbs were generated that specifically recognize human GARP as determined by flow cytometry (FIG. 7A). All of these clones were specific for human GARP with the exception of one clone, 4D3, that had a low level of cross-reactivity against mouse GARP. 4D3 was the only clone able to block the binding of exogenous human LTGFβ-1 (huLTGFβ-1) to surface GARP (FIG. 7B). To examine if GARP antibody had any direct anti-tumor activities in vivo, BALB/c mice were inoculated orthotopically with human GARP-expressing 4T1 tumor cells. Mice were then treated with either 4D3 (IgG1) or a second anti-GARP mAb 5C5 (IgG2a), or with isotype control antibody (ISO), either with or without a single dose of CY. This regimen was chosen because it was shown previously that a TGF-β-neutralizing antibody 1D11 was able to potentiate the ability of CY to control 4T1 (Chen et al., 2014). It was found that both 4D3 and 5C5 treatment modestly inhibited primary tumor growth (FIG. 7C). More importantly, however, tumor metastasis to the lungs was significantly decreased in the anti-GARP mAb treatment groups compared with the isotype-treated group, regardless of concomitant treatment with chemotherapy (FIG. 7D). Noticeably, treatment with 4D3, which blocks the binding of LTGF-β to GARP, was also associated with a significant reduction in splenic Tregs and Gr1$^+$CD11b$^+$ myeloid-derived suppressor cells (MDSCs) (FIG. 7E).

Figures 8A, 8B, 8C, 8D, 8E, 8F:
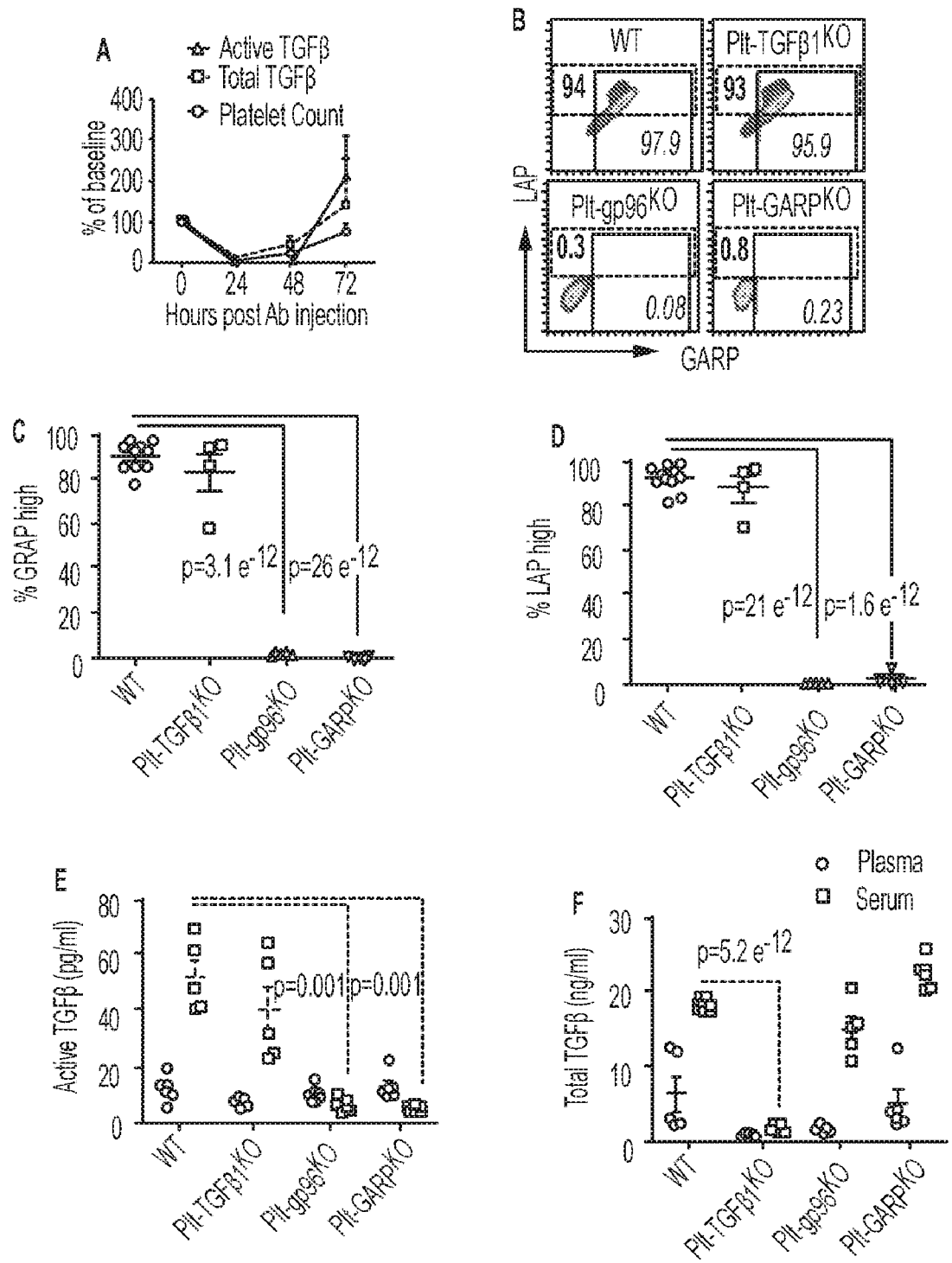
FIGS. 8A-8F. Platelet-intrinsic GARP plays critical roles in generating active TGFβ. (8A) Depletion of platelets resulted in a complete loss of active and total TGFβ. (8B-8D) Expression of GARP and LAP in indicated mouse models. Platelets from Plt-Tgfβ1KO mice express similar levels of surface GARP-TGFβ1 complex when compared with WT platelets. (8E) Measure of active TGFβ in mice. In WT mice, active TGFβ is elevated in serum compared to plasma. (8F) Measure of total TFGβ in mice. The total latent TGFβ level in the serum is reduced in Plt-Tgfβ1KO mice but not Plt-gp96KO or Plt-GARPKO mice.

Platelets not only produce and store high levels of TGFβ intracellularly, but also are the only cellular entity known so far that constitutively expresses cell surface docking receptor GARP for TGFβ. Thus, platelets may contribute to the systemic levels of TGFβ via active secretion as well as GARP-mediated capturing from other cells or the extracellular matrix. To what extent and how platelets contribute to the physiological TGFβ pool were addressed. Baseline sera were obtained from wild type (WT) mice followed by administration of a platelet depleting antibody. These mice were sequentially bled and serum TGFβ was quantified by ELISA. Depletion of platelets resulted in a complete loss of active and total TGFβ, which rebounded effectively as soon as platelet count recovered (FIG. 8A). These experiments demonstrate that platelets contribute dominantly to the circulating TGFβ level.

The biology of platelet-derived TGFβ in cancer immunity was experimentally addressed by focusing on the role of platelet GARP in the production of active TGFβ. In addition to platelet-specific Hsp90b1 KO mice, two additional mouse models were generated: One with selective deletion of GARP in platelets (Pf4-cre-Lrrc32flox/flox, or Plt-GARPKO) and another with platelet-restricted knockout of TGFβ1 (Pf4-cre-Tgfb1flox/flox or Plt-Tgfβ1KO). As gp96 is also an obligate chaperone for GARP, platelets from neither Plt-gp96KO mice nor Plt-GARPKO mice expressed cell surface GARP-TGFβ complex. Platelets from Plt-Tgfβ1KO mice, however, expressed similar levels of surface GARP-TGFβ1 complex when compared with WT platelets (FIGS. 8B-8D), indicating that the GARP-TGFβ1 complex can be formed without autocrine TGFβ1.

The levels of active and latent TGFβ were then measured in the plasma and sera of WT and knockout mice (FIG. 8E, F). In WT mice, active TGFβ was elevated in serum compared to plasma, indicating a role for platelets and/or the coagulation cascade in TGFβ activation (FIG. 8E). Importantly, Plt-gp96KO and Plt-GARPKO mice had very little active TGFβ in their sera, confirming the importance of platelet-intrinsic GARP in converting latent TGFβ to the active form. In contrast, the serum level of active TGFβ in Plt-Tgfβ1KO mice was comparable to that of WT mice (FIG. 8E), indicating that platelets are capable of activating TGFβ from non-platelet sources in a trans fashion. Significantly, the total latent TGFβ level in the serum is only reduced in Plt-Tgfβ1KO mice but not Plt-gp96KO or Plt-GARPKO mice (FIG. 8F). Collectively, these data indicate that platelet-intrinsic GARP is the most important mechanism in the activation of TGFβ systemically. This experiment also categorically confirmed that serum but not plasma level of active TGFβ reflects exclusively platelet activation.

Figures 9A, 9B, 9C, 9D:
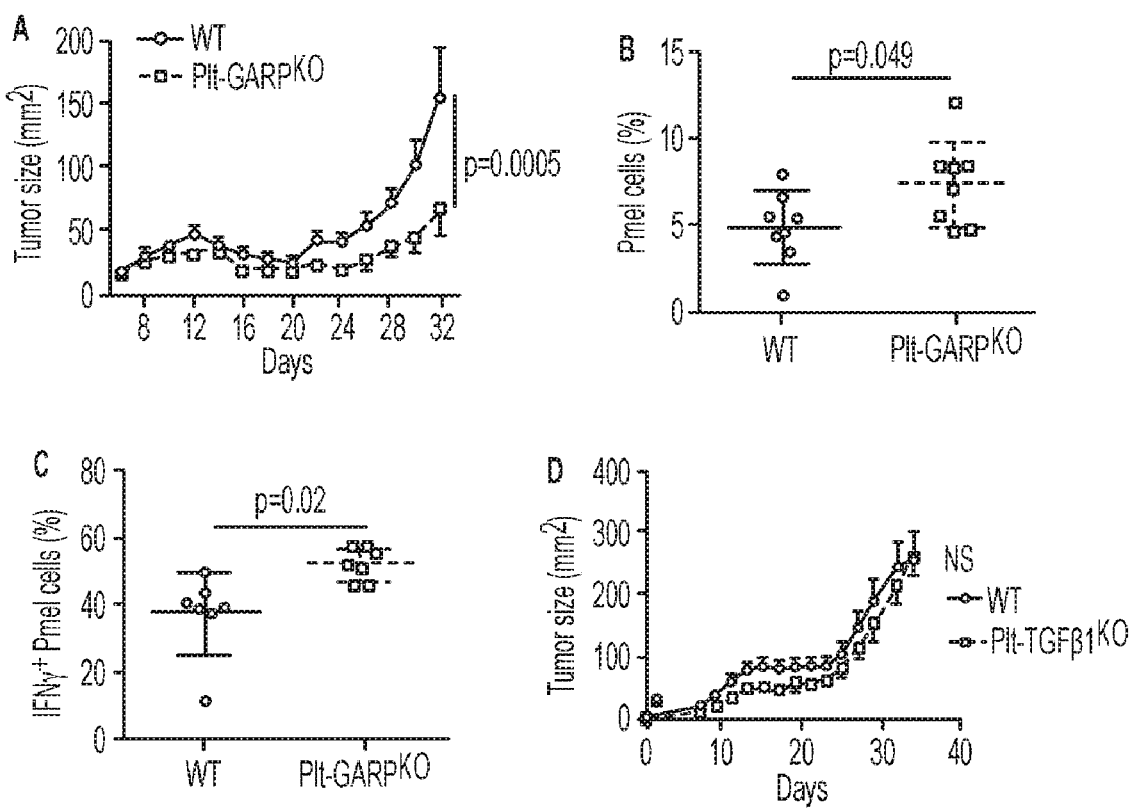
FIGS. 9A-9D. Efficacy of adoptive T cell therapy of melanoma in WT, Plt-Tgfβ1KO and Plt-GARPKO recipient mice. (9A) Tumor growth is controlled more efficiently in Plt-GARPKO mice compared with WT mice. (9B) Enhanced persistence and (9C) functionality of Pmel cells in peripheral blood of Plt-GARPKO mice. (9D) Plt-Tgfβ1KO mice, whose platelets express GARP and remain capable of activating TGFβ, do not have improved control of tumors.
Figures 10A, 10B, 10C, 10D, 10E, 10F, 10G, 10H:
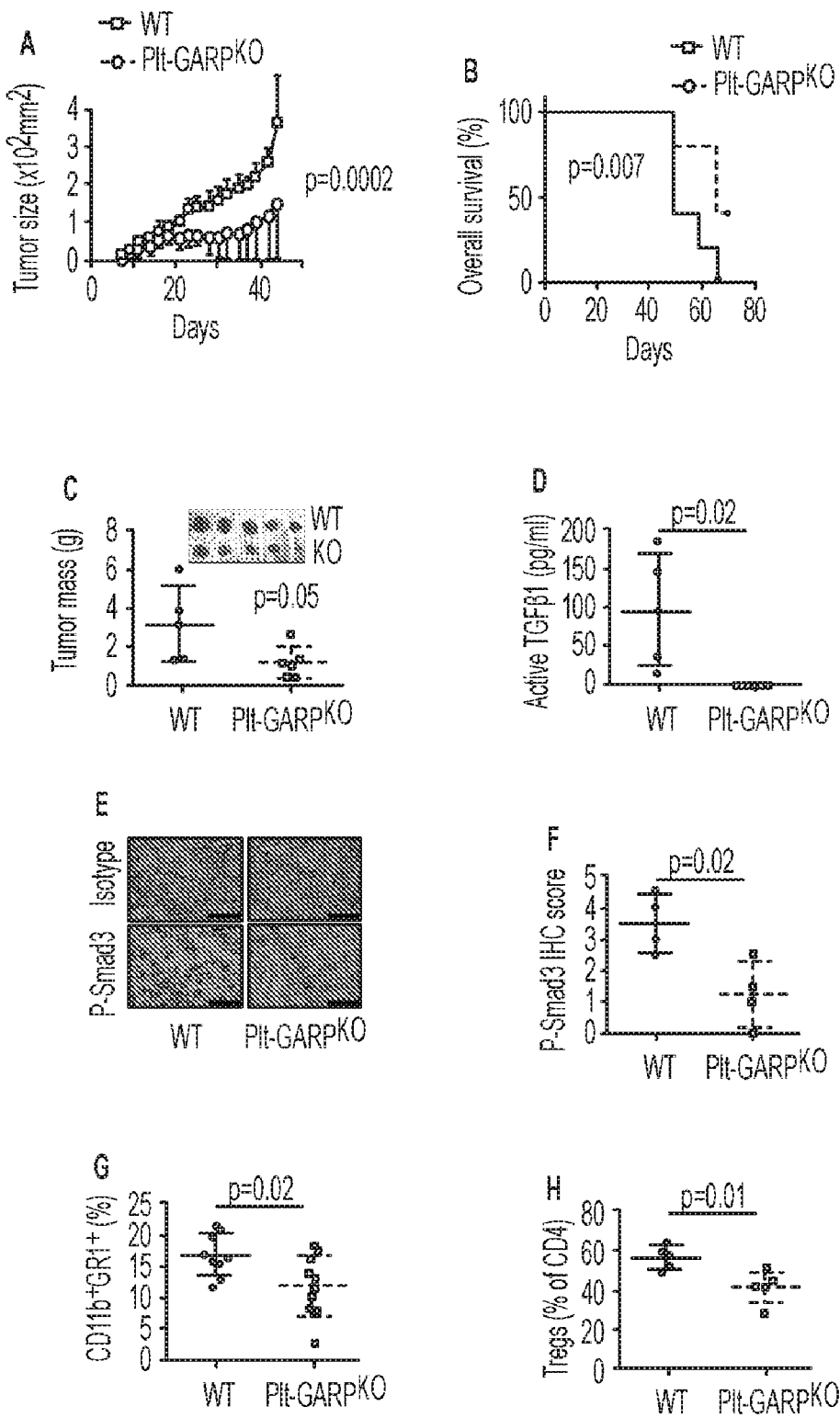
FIGS. 10A-10H. Platelet-derived GARP-TGFβ complex blunts anti-tumor T cell immunity. (10A-10C) Tumor size (10A) and overall survival of WT and Plt-GARPKO mice. The growth of MC38 is significantly diminished in Plt-GARPKO mice compared to WT mice. (10D) MC38-bearing Plt-GARPKO mice have reduced serum levels of active TGFβ. (10E-10F) Immunohistochemical staining for p-Smad2/3 (p-Smad2/3) in MC38 tumor sections demonstrates a remarkable attenuation of TGFβ signaling in MC38 cells in Plt-GARPKO mice. (10G) Reduction of both systemic myeloid-derived suppressor cells (10H) and tumor-infiltrating regulatory T cells in Plt-GARPKO mice.

It is hypothesized that platelet-specific GARP play critically negative roles in anti-tumor T cell immunity. This hypothesis was addressed by comparing the efficacy of adoptive T cell therapy of melanoma in WT, Plt-Tgfβ1KO and Plt-GARPKO recipient mice (FIG. 9). B16-F1 melanomas were established in either WT or KO mice, followed by lymphodepletion with cyclophosphamide (Cy) on day 9, and the infusion of ex vivo activated Pmel T cells on day 10 (FIG. 9A). Tumors were controlled much more efficiently in the Plt-GARPKO mice compared with WT mice (FIG. 9A). This was associated with enhanced persistence (FIG. 9B) and functionality of Pmel cells in the peripheral blood of Plt-GARPKO mice (FIG. 9C). In stark contrast, Plt-Tgfβ1KO mice, whose platelets express GARP and remain capable of activating TGFβ, did not have improved control of tumors (FIG. 9D). The generality of these findings were next studied in the MC38 colon carcinoma system given that the growth of this transplantable tumor in syngeneic mice undergoes both CD4 and CD8-mediated immune pressure. The growth of MC38 was significantly diminished in Plt-GARPKO mice compared to WT mice (FIGS. 10A-10C). The MC38-bearing Plt-GARPKO mice had reduced serum levels of active TGFβ (10D). More importantly, staining for p-Smad2/3 (p-Smad2/3) in MC38 tumor sections demonstrated a remarkable attenuation of TGFβ signaling in MC38 cells in Plt-GARPKO mice (FIGS. 10E and 10F). This was associated with reduction of both systemic myeloid-derived suppressor cells (FIG. 10G) and tumor-infiltrating regulatory T cells in Plt-GARPKO mice (FIG. 10H). Taken together, this demonstrates that platelets are the commanding source of TGFβ activity in the tumor microenvironment and they exert potent immunosuppressive effects on anti-tumor immunity via GARP-TGFβ.

Figures 11A, 11B, 11C, 11D:
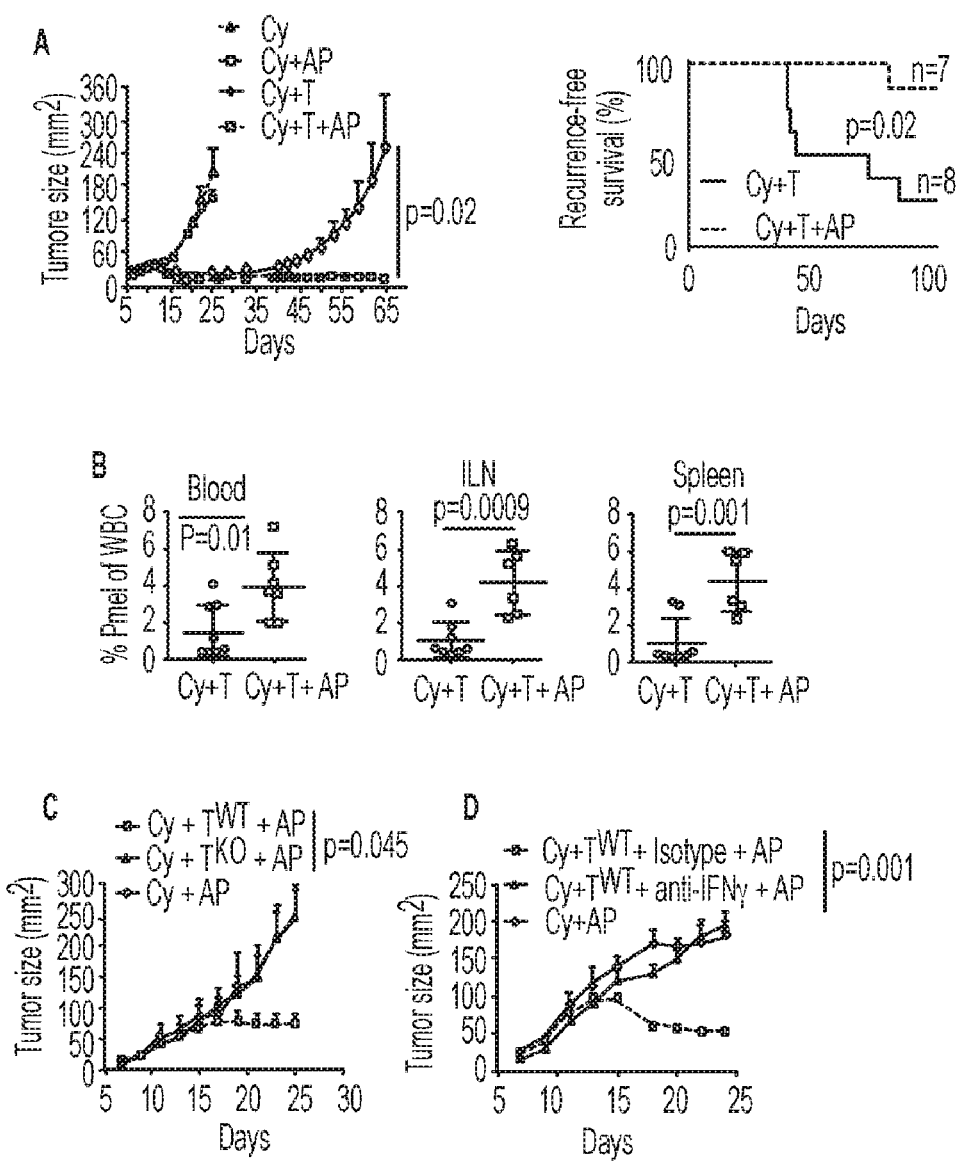
FIGS. 11A-11D. Anti-platelet pharmacological agents potentiate adoptive T cell therapy of cancer. (11A) Effect of Cy and AP on tumor growth (left). Anti-platelet agents plus adoptive T cell transfer are highly effective against B16-F1 with relapse-free survival of most mice beyond 3 months (right). (11B) Antigen-specific T cells sustained at higher numbers in the blood, inguinal lymph nodes (ILNs) and spleens of mice receiving concurrent anti-platelet therapy and ACT. (11C) Antiplatelet agents conferred no benefit when the transferred T cells lacked IFNgamma (11D) or when anti-IFNgamma neutralization antibodies were administered.

To establish the clinical relevance of the suppressive effect of platelets on anti-tumor immunity, the impact of platelets on immunotherapy was addressed pharmacologically. B16-F1 melanomas were established in C57BL/6 mice after subcutaneous injection on day 0, followed by lymphodepletion with Cy on day 7, and infusion of ex vivo primed Pmel cells on day 8, along with anti-platelet (AP) agents: aspirin and clopidogrel. Aspirin and clopidogrel inhibit platelet activation by blocking cycloxyenase and ADP receptors, respectively. Cy alone failed to control tumors, and the additional AP also had no anti-tumor effects in this model (FIG. 11A, left panel). Melanoma was controlled well with T cells plus Cy for about one month, but most mice eventually relapsed. In contrast, anti-platelet agents plus adoptive T cell transfer were highly effective against B16-F1 with relapse-free survival of most mice beyond 3 months (FIG. 11A, right panel). As a further proof, antigen-specific T cells were sustained at higher numbers in the blood, inguinal lymph nodes (ILNs) and spleens of mice receiving concurrent anti-platelet therapy and ACT (FIG. 11B). Importantly, antiplatelet agents conferred no benefit when the transferred T cells lacked IFNgamma (FIG. 11C) or when anti-IFNgamma neutralization antibodies were administered (FIG. 11D), demonstrating that the effects of anti-platelet agents were immune-mediated.

Example 5

Materials and Methods

Cell lines and mice. Pre-B cell line (70Z/3) was a kind gift from Brian Seed (Harvard University) (Randow and Seed, 2001). The 4T1 mouse mammary epithelial cell cancer line, wild-type (WT) normal murine mammary gland epithelial cells (NMuMG) and NMuMG* subline with silencing of hnRNP E1 were described previously (Hussey et al., 2011). B16-F1 and 293FT cell lines were purchased from ATCC.

6-8 weeks old female BALB/c, C57BL/6J, NOD-Rag$^{-/-}$, NSG breeder pairs (NOD Scid Gamma) and Pmel 1 T cell receptor (TCR) transgenic (Tg) mice were purchased from The Jackson Laboratory (Bar Harbor, Me. USA). All animal experiments involving mice were approved by Medical University of South Carolina's Institutional Animal Care and Use Committee, and the established guidelines were followed. Control and treated mice were co-housed, and 6-8 weeks old female age-matched mice were used in all experiments.

Tissue microarrays and human serum. All human tumor microarrays (TMAs) were made out of formalin-fixed, paraffin embedded tissues. Colon, lung and one of two breast cancer TMAs were developed from specimens collected at the Medical University of South Carolina (MUSC Charleston, S.C.). Each patient specimen in these TMAs was represented in two cores on the slide and each core measured 1 mm in diameter. TMAs for breast and prostate cancers were purchased commercially from imgenex, Inc (San Diego. Calif.). These patient specimens were available in a single core of 2 mm in diameter, Clinical and demographic information were obtained from the Cancer Registry of the Hollings Cancer Center at MUSC or provided by the commercial source. This study was approved by the Institutional Review Board (IRB) at MUSC.

Immunohistochemistry (IHC). The mouse anti-human GARP antibody used in this study (ALX-804-867-C100, Enzo Life Sciences) was first tested by Western blot in untransfected and hGARP-transfected Human Embryonic Kidney (HEK)-293 cells and by IHC using hGARP-transfected and control vector-transfected mouse Pre-B leukemic cells 70Z/3. Both analyses demonstrated specificity of the antibody and dilutions used from 1:250 (colon cancer) to 1:60 (all other cancers).

TMA slides were baked for 2 h at 62° C., followed by de-paraffinization in xylenes and rehydration. Antigen retrieval was then performed by boiling in citrate buffer (pH=6.0) for 30 min in a steamer. Slides were incubated in 3% $H_2O_2$ in dH2O for 7 min and non-specific binding was blocked by 2% normal horse serum for 2 h at room temperature. Samples were incubated with anti-h-GARP antibody at 4° C. for 16 h, followed by secondary antibody (Vectastain ABC Kit) and development using DAB substrate (Vector Labs SK-4100). Staining was specific to the cytoplasm and cell membrane, with negative nuclear staining.

For mouse IHC, primary tumors and lungs were isolated. Tumor tissue was either placed into OCT media for fresh frozen sections or fixed in 4% paraformaldehyde overnight for fixed sections. For hematoxylin and eosin (H&E) analysis of the tumor and lungs, fixed tissue was incubated in 70% ethanol overnight prior to paraffin embedding, and then cut for H&E staining. For p-Smad-2/3 on fresh frozen tumor sections, 5 μm sections were fixed with 4% paraformaldehyde followed by incubation with 3% $H_2O_2$. To minimize nonspecific staining, sections were incubated with the appropriate animal serum for 20 min at room temperature, followed by incubation with primary anti-p-Smad-2/3 (EP823Y; Abcam) overnight at 4° C. Standard protocol of anti-rat Vectastain ABC Kil (Vector Labs) was followed.

The staining intensity of GARP and pSmad-2/3 was graded by a board-certified pathologist (S.S.) with the sample identity blinded (0: negative; 1: faint, 2: moderate; 3: strong but less intense than 4; and 4: intense). Percentage of positive cells per patient sample in the TMA was also calculated; in TMAs where specimens where spotted in duplicates, the average of both cores was used as the representative value. Student t-test was implemented to compare categorical variables like normal versus cancer or different disease stages or categories. Kaplan-Meier analysis for correlation of GARP with survival was performed using X-tile software (Camp et al., 2004). Population characteristics were tested for statistically significant differences between low and high GARP expressers using Chi-squared test.

Immunofluorescence analysis. Fresh frozen tumor cryosections (5 μm) were air-dried, fixed in acetone for 10 min and then incubated with Phycoerythrin conjugated anti-CD31 antibody (1:50). Vessel density was determined by calculating the area of CD31 staining using an ImageJ v1.34 software program (NIH) after imaging on an Olympus fluorescent microscope.

GARP knockdown by lentivirus-expressed short hairpin RNA. A lentivirus vector-expressing short hairpin RNA (shRNA) targeting the mouse GARP transcript was purchased from Sigma-Aldrich (St. Louis, Mo.). Ecotropic GARP shRNA and control scrambled lentiviral shRNA particles were produced in HEK293FT cells as described previously (Hong et al., 2013; Wu et al., 2012). To knock down GARP in NMuMG* cells, the cells were transduced with lentiviral supernatants targeting GARP and scrambled control. The knockdown efficiency was assessed by RT-PCR (Applied Biosystems Step-One Plus) and flow cytometry (BD Verse) using an anti-mouse GARP antibody (eBioscience).

Generation of GARP-expression vectors. GARP was amplified by PCR and subcloned between the BglII and HpaI sites in a MigR1 retroviral vector. A cDNA construct for expression of the recombinant GARP-Fc fusion protein was generated by joining the extracellular domain of GARP sequence to the sequence encoding the Fc portion of murine IgG2a constant region. The Fc sequence was amplified by PCR from the phCMV1 vector and GARP was amplified using PCR from MigR1 retroviral vector. The two fragments were ligated and cloned into the MigR1 retroviral expression vector. Ecotropic GARP and GARP-Fc retroviral particles were packaged into the Pheonix-Ecotropic cells. Virus propagation and transduction of Pre-B cells, 4T1 cells and NMuMG* cells were based on the established protocols (Wu et al., 2012; Zhang et al., 2015). Cells were stably selected by culturing in presence of blasticidin 48 h post transduction for at least 72 h.

Purification of GARP-Fc. For purification of GARP-Fc protein GARP-Fc, MigR1 vector was transfected into Chinese hamster ovary (CHO) cells using Lipofectamine 2000 (Invitrogen) according to the manufacturer's instructions. Stably transfected clones were selected by blasticidin (5 µg/ml) and protein expression was quantified by SDS-PAGE and Western blot under reducing conditions using anti-mouse GARP and anti-mouse Fc antibody. Recombinant GARP-Fc was purified from cell culture supernatants by protein A affinity chromatography (GE Health).

Generation and characterization of anti-GARP antibody. Four BALB/c mice were immunized with recombinant human GARP (R&D Systems, Minneapolis, Minn.) with Freund's complete adjuvant, followed by boosting with SP2/0 cells stably expressing human GARP for 2-3 times. Splenic B cells from mice with high anti-GARP antibody titers were fused to SP2/0 cells in the presence of polyethylene glycol. Hybridomas were selected in HAT medium and cloned by limiting dilution assay. The specificity of antibody was screened and determined by ELISA and flow cytometry using 70Z/3 cells stably transduced with empty vector (70Z/3-EV) and overexpression of human GARP (70Z/3-GARP).

Protein extraction, immunoprecipitation, and Western blot analysis. Cells were harvested by trypsin-EDTA when necessary, washed in PBS, and lysed on ice in radio-immunoprecipitation assay (RIPA) lysis buffer in the presence of a protease inhibitor cocktail (Sigma-Aldrich). Nuclear-free protein lysate was quantified by Bradford assay (Bio-Rad), and an equal amount of lysate was analysed by SDS-PAGE and Western blot under reducing conditions using anti-mouse GARP (AF6229; R&D system), anti-mouse Vimentin (D21H3; Cell signaling), anti-mouse E-Cadherin (24E10; Cell Signaling) and anti-mouse p-Smad-2/3 (EP823Y; Abcam).

Cell proliferation and in vitro wound healing assay. NMuMG cells ($4 \times 10^5$) were starved overnight in serum free DMEM (Corning cellgro). Starved cells were cultured at the indicated times with GARP-Fc in 2% FBS DMEM. To measure cell proliferation, $2.5 \times 10^4$ cells were seeded in a 96-well plate in complete medium (DMEM, 10% FCS, 1% penicillin-streptomycin) and incubated overnight. Proliferation was determined with 3-[4,5 dimethylthiazol-2-yl]-2,5-diphenyltetrazolium bromide (MTT), which was added to the cells at the indicated times and incubated for an additional 3 h at 37° C. The medium was then removed and mixed with 100 µl of DMSO for 15 minutes by shaking. Absorbance at 570 nm was then measured using a plate reader. The cell migration was measured by the wound-healing assay: at 100% confluence, two parallel wounds were made using a 1 ml pipette tip. Migration was assessed after 24, 48 and 72 hours and quantification of wound closure was measured using the ImageJ software (NIH).

4T1 Tumor model and GARP antibody therapy. Female BALB/c mice, 6-8-week old were inoculated in the fourth mammary fat pad subcutaneously (s.q.) with $5 \times 10^5$ cells (4T1 EV, 4T1 GARP, or 4T1 GARP-Fc). Tumor growth was monitored three times per week with a digital vernier caliper and tumor volume was calculated using the following formula: tumor volume $(mm^3) = [(width)^2 \times length]2$. In GARP antibody therapy experiments, beginning at 3 days post-tumor inoculation, anti-GARP antibody or polyclonal iso-type-controlled antibody (0.1 mg/mouse in 0.1 mL PBS; three times per week) were administered intraperitoneally (i.p.) into mice. For combination therapy with cyclophosphamide (CY) and antibody, mice were treated with one injection of CY (4 mg/mouse) 3 days post-tumor inoculation in addition to the antibody treatment. At end-point, mice were sacrificed and the primary tumor, draining LNs, spleen, lungs and liver were isolated. Tumor infiltrated lymphocytes were isolated by Collagenase D (Sigma) digestion followed by Histopaque-1083 (Sigma) mediated density separation.

B16-F1 tumor model and adoptive T cell therapy (ACT). Three groups (B16 EV, and B16 GARP-Fc; n=5-7 each group) of 6-8-week old female C57BL/6J mice were inoculated s.q. in the right flank using $2.5 \times 10^5$ cells and, when specified, treated with one intra-peritoneal injection of CY (4 mg/mouse) a day prior to adoptive T cell therapy. To obtain gp100-specific T cells, the splenocytes from Pmel TCR transgenic female mouse were stimulated with hgp100 (25-33 epitope, 1 µg/ml, American peptide Company) and mouse IL-12 (10 ng/ml, Shenandoa) for 3 days. ACT was done via tail vein injection of $2 \times 10^6$ activated Pmel T cells per recipient mouse a day after injection of CY. Primary tumor growth was monitored 3 times per week with vernier calipers. Peripheral adoptively transferred Pmel cells were monitored at 2, 3, 4, and 5 weeks after ACT. Ex-vivo Pmel IFN-γ production was assess stimulating Pmel cells for 3 h in presence of hgp100 and brefeldin A (BFA) at 37° C. and analyzed by flow cytometry.

NMuMG tumor model. Female NOD-Rag-1$^{-/-}$ (n=5 each group; 6-8 week old) mice were inoculated in the fourth and left mammary fat pad subcutaneously using $5 \times 10^5$ cells (NMuMG*-EV, GARP knockdown NMuMG*). Animals were weighed and tumors measured weekly. At endpoint, primary tumors, lungs and livers were harvested. In another experiment, female NOD-Rag-1$^{-/-}$ mice (n=4-5 each group; 6-8 week old) were inoculated in the fourth left mammary fat pad subcutaneously with $5 \times 10^5$ cells (NMuMG-GARP-Luc, NMuMG-GARP-Fc-Luc or NMuMG-Luc cells). In vivo luciferase imaging was evaluated weekly as follows: mice were intraperitoneally injected with D-luciferin (Perkin Elmer) at a dose of 150 mg/kg per mouse and anesthetized. Bioluminescence images were then acquired using Xenogen IVIS imaging system. Bioluminescence signal was quantified as photon flux (photons/s/cm$^2$) in defined regions of interest using Living Image software (Xenogen).

TGF-β1, GARP, and GARP-TGF-β1 analysis. Active TGF-β1, total TGF-β1, and soluble GARP were measured in human and mouse serum using TGF-β1 and GARP ELISA kits (BioLegend, San Diego, Calif.) according to the manufacturer's protocols. To measure GARP-TGF-β1 complex by ELISA, 96-well plates were coated with TGF-β1 capture antibody according to the manufacturer's instructions (BioLegend, San Diego, Calif.). Samples were incubated for 2 h at room temperature followed by the incubation with the anti-hGARP detection antibody developed in our lab for another 2 h.

For MFB-F11 functional assay, MFB-F11 cells (a kind gift from Tony Wyss-Coray, Stanford University) were cultured in DMEM with 10% FBS and 1% penicillin/strepomycin. $2\times10^4$ cells were seeded per well and incubated overnight. Prior to addition of diluted serum or tumor supernatant, cells were serum starved for 2-3 hours. Diluted serum or tumor supernatant samples were incubated for 24 hours, followed by analysis using QUANTI-Blue Medium (InvivoGen, San Diego, Calif.) (Tesseur et al., 2006).

Statistical Analysis. In TMAs where specimens were spotted in duplicate, the average of both cores was used as the representative value. Student t-test was implemented to compare categorical variables such as normal versus cancer or different disease stages or categories. Kaplan-Meier analysis for correlation of GARP with survival was performed using X-tile software (Camp et al., 2004). Population characteristics were tested for statistically significant differences between low and high GARP expressers using Chi-squared test. Tumor curve analysis was performed using 2-way analysis of variance (ANOVA); all other experiments were analyzed using Two-tailed Student T-test with GraphPad Prism. All data are presented as mean±SEM. P values less than 0.05 were considered to be statistically significant.

Example 6

Antibodies Against GARP (LRRC32)

apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahn, Y. O., Lee, J. C., Sung, M. W., and Heo, D. S. (2009). Presence of membrane-bound TGF-beta1 and its regulation by IL-2-activated immune cell-derived IFN-gamma in head and neck squamous cell carcinoma cell lines. Journal of immunology 182, 6114-6120.

Akhurst, R. J., and Hata, A. (2012). Targeting the TGF-beta signalling pathway in disease. Nature reviews Drug discovery 11, 790-811.

Baker, K., Raut, P., and Jass, J. R. (2008). Colorectal cancer cells express functional cell surface-bound TGFbeta. International journal of cancer Journal international du cancer 122, 1695-1700.

Beyer, M., and Schultze, J. L. (2006). Regulatory T cells in cancer. Blood 108, 804-811.

TABLE 1

GARP monoclonal antibody clones

| mAb | Heavy Chain Sequence | | | Light Chain Sequence | | |
|---|---|---|---|---|---|---|
| | CDR1 | CDR2 | CDR3 | CDR1 | CDR2 | CDR3 |
| | Amino acid sequence | | | Amino acid sequence | | |
| 4d3 | GYSITSDYA (SEQ ID NO: 1) | ISYSGST (SEQ ID NO: 2) | AKSGGDYY GSSSYWYF DV (SEQ ID NO: 3) | QSLLNSRS QKNY (SEQ ID NO: 5) | RAS (SEQ ID NO: 6) | QNDHSYPFT (SEQ ID NO: 7) |
| | LDVQLQESGPGLVKPSQSLSLTCTVTG YSITSDYAWNWIRQFPGNKLEWMGYIS YSGSTSYTPSLKSRISITRDTSKNHFF LQSNSVTTEDTATYYCAKSGGDYYGSS SYWYFDVWGAGTTVTVSS (SEQ ID NO: 4) | | | DIQMTQSPSSLSVSAGEKVTMSCKSSQ SLLNSRSQKNYLAWYQQKPGQPPKLLI YRASTRGSGVPDRFTGSGSGTDFTLTI SSVQAEDLAVYYCQNDHSYPFTFGSGT KLEIK (SEQ ID NO: 8) | | |
| 5c5 | GFTFSNYV (SEQ ID NO: 9) | ISSGGSY T (SEQ ID NO: 10) | ARGYDNGD YVMDY (SEQ ID NO: 11) | ESVDTYGN SF (SEQ ID NO: 13) | RAS (SEQ ID NO: 14) | QQTNEHPPT (SEQ ID NO: 15) |
| | EVKLVESGGGSVKPGGSLKLSCAASGF TFSNYVMSWVRQTPEKRLEWVATISSG GSYTYYPDSVKGRLTISRDNAKNTLYL QMSSLRSEDTAMYYCARGYDNGDYVMD YWGQGTSVTVSS (SEQ ID NO: 12) | | | DIVLTQSPASLAVSLGQRATISCRASE SVDTYGNSFMHWYQQIPGQPPKVLIYR ASNLESGIPARFSGSGSRTDFTLTINP VEAGDVATYYCQQTNEHPPTFGGGTKL EIK (SEQ ID NO: 16) | | |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications Bhowmick, N. A., Ghiassi, M., Bakin, A., Aakre, M., Lundquist, C. A., Engel, M. E., Arteaga, C. L., and Moses, H. L. (2001). Transforming growth factor-beta1 mediates epithelial to mesenchymal transdifferentiation through a RhoA-dependent mechanism. Molecular biology of the cell 12, 27-36.

Camp, R. L., Dolled-Filhart, M., and Rimm, D. L. (2004). X-tile: a new bio-informatics tool for biomarker assessment and outcome-based cut-point optimization. Clinical cancer research: an official journal of the American Association for Cancer Research 10, 7252-7259.

Carrillo-Galvez, A. B., Cobo, M., Cuevas-Ocana, S., Gutierrez-Guerrero, A., Sanchez-Gilabert, A., Bongarzone, P., Garcia-Perez, A., Munoz, P., Benabdellah, K., Toscano, M. G., et al. (2015). Mesenchymal stromal cells express GARP/LRRC32 on their surface: effects on their biology and immunomodulatory capacity. Stem cells 33, 183-195.

Chen, X., Yang, Y., Zhou, Q., Weiss, J. M., Howard, O. Z., McPherson, J. M., Wakefield, L. M., and Oppenheim, J. J. (2014). Effective chemoimmunotherapy with anti-TGFbeta antibody and cyclophosphamide in a mouse model of breast cancer. PloS one 9, e85398.

Cuende, J., Lienart, S., Dedobbeleer, O., van der Woning, B., De Boeck, G., Stockis, J., Huygens, C., Colau, D., Somja, J., Delvenne, P., et al. (2015). Monoclonal antibodies against GARP/TGF-beta1 complexes inhibit the immunosuppressive activity of human regulatory T cells in vivo. Science translational medicine 7, 284ra256.

Derynck, R., Akhurst, R. J., and Balmain, A. (2001). TGF-beta signaling in tumor suppression and cancer progression. Nature genetics 29, 117-129.

Edwards, J. P., Fujii, H., Zhou, A. X., Creemers, J., Unutmaz, D., and Shevach, E. M. (2013). Regulation of the expression of GARP/latent TGF-beta1 complexes on mouse T cells and their role in regulatory T cell and Th17 differentiation. Journal of immunology 190, 5506-5515.

Flavell, R. A., Sanjabi, S., Wrzesinski, S. H., and Licona-Limon, P. (2010). The polarization of immune cells in the tumour environment by TGFbeta. Nature reviews Immunology 10, 554-567.

Gauthy, E., Cuende, J., Stockis, J., Huygens, C., Lethe, B., Collet, J. F., Bommer, G., Coulie, P. G., and Lucas, S. (2013). GARP is regulated by miRNAs and controls latent TGF-beta1 production by human regulatory T cells. PloS one 8, e76186.

Hahn, S. A., Stahl, H. F., Becker, C., Correll, A., Schneider, F. J., Tuettenberg, A., and Jonuleit, H. (2013). Soluble GARP has potent antiinflammatory and immunomodulatory impact on human CD4(+) T cells. Blood 122, 1182-1191.

Hong, F., Liu, B., Chiosis, G., Gewirth, D. T., and Li, Z. (2013). alpha7 Helix Region of alpha1 Domain Is Crucial for Integrin Binding to Endoplasmic Reticulum Chaperone gp96: A POTENTIAL THERAPEUTIC TARGET FOR CANCER METASTASIS. The Journal of biological chemistry 288, 18243-18248.

Howley, B. V., Hussey, G. S., Link, L. A., and Howe, P. H. (2015). Translational regulation of inhibin betaA by TGFbeta via the RNA-binding protein hnRNP E1 enhances the invasiveness of epithelial-to-mesenchymal transitioned cells. Oncogene.

Hussey, G. S., Chaudhury, A., Dawson, A. E., Lindner, D. J., Knudsen, C. R., Wilce, M. C., Merrick, W. C., and Howe, P. H. (2011). Identification of an mRNP complex regulating tumorigenesis at the translational elongation step. Molecular cell 41, 419-431.

Huygens, C., Lienart, S., Dedobbeleer, O., Stockis, J., Gauthy, E., Coulie, P. G., and Lucas, S. (2015). Lysosomal-associated Transmembrane Protein 4B (LAPTM4B) Decreases Transforming Growth Factor beta1 (TGF-beta1) Production in Human Regulatory T Cells. The Journal of biological chemistry 290, 20105-20116.

Kehrl, J. H., Wakefield, L. M., Roberts, A. B., Jakowlew, S., Alvarez-Mon, M., Derynck, R., Sporn, M. B., and Fauci, A. S. (1986). Production of transforming growth factor beta by human T lymphocytes and its potential role in the regulation of T cell growth. The Journal of experimental medicine 163, 1037-1050.

Kopp, H. G., Placke, T., and Salih, H. R. (2009). Platelet-derived transforming growth factor-beta down-regulates NKG2D thereby inhibiting natural killer cell antitumor reactivity. Cancer research 69, 7775-7783.

Li, M. O., and Flavell, R. A. (2008). TGF-beta: a master of all T cell trades. Cell 134, 392-404.

Li, Y., Kim, B. G., Qian, S., Letterio, J. J., Fung, J. J., Lu, L., and Lin, F. (2015). Hepatic Stellate Cells Inhibit T Cells through Active TGF-beta1 from a Cell Surface-Bound Latent TGF-beta1/GARP Complex. Journal of immunology 195, 2648-2656.

Lyons, R. M., Gentry, L. E., Purchio, A. F., and Moses, H. L. (1990). Mechanism of activation of latent recombinant transforming growth factor beta 1 by plasmin. J Cell Biol 110, 1361-1367.

Massague, J. (2008). TGFbeta in Cancer. Cell 134, 215-230.

Muranski, P., Boni, A., Antony, P. A., Cassard, L., Irvine, K. R., Kaiser, A., Paulos, C. M., Palmer, D. C., Touloukian, C. E., Ptak, K., et al. (2008). Tumor-specific Th17-polarized cells eradicate large established melanoma. Blood 112, 362-373.

Oft, M., Heider, K. H., and Beug, H. (1998). TGFbeta signaling is necessary for carcinoma cell invasiveness and metastasis. Curr Biol 8, 1243-1252.

Ollendorff, V., Noguchi, T., deLapeyriere, O. and Birnbaum, D. (1994). The GARP gene encodes a new member of the family of leucine-rich repeat-containing proteins. Cell growth & differentiation: the molecular biology journal of the American Association for Cancer Research 5, 213-219.

Overwijk, W. W., Theoret, M. R., Finkelstein, S. E., Surman, D. R., de Jong, L. A., Vyth-Dreese, F. A., Dellemijn, T. A., Antony, P. A., Spiess, P. J., Palmer, D. C., et al. (2003). Tumor regression and autoimmunity after reversal of a functionally tolerant state of self-reactive CD8+ T cells. The Journal of experimental medicine 198, 569-580.

Padua, D., Zhang, X. H., Wang, Q., Nadal, C., Gerald, W. L., Gomis, R. R., and Massague, J. (2008). TGFbeta primes breast tumors for lung metastasis seeding through angiopoietin-like 4. Cell 133, 66-77.

Pertovaara, L., Kaipainen, A., Mustonen, T., Orpana, A., Ferrara, N., Saksela, O., and Alitalo, K. (1994). Vascular endothelial growth factor is induced in response to transforming growth factor-beta in fibroblastic and epithelial cells. J Biol Chem 269, 6271-6274.

Pulaski, B. A., and Ostrand-Rosenberg, S. (2001). Mouse 4T1 breast tumor model. Current protocols in immunology/edited by John E Coligan [et al] *Chapter* 20, Unit 20 22.

Randow, F., and Seed, B. (2001). Endoplasmic reticulum chaperone gp96 is required for innate immunity but not cell viability. Nature cell biology 3, 891-896.

Roberts, A. B., Sporn, M. B., Assoian, R. K., Smith, J. M., Roche, N. S., Wakefield, L. M., Heine, U. I., Liotta, L. A., Falanga, V., Kehrl, J. H., et al. (1986). Transforming growth factor type beta: rapid induction of fibrosis and angiogenesis in vivo and stimulation of collagen formation in vitro. Proceedings of the National Academy of Sciences of the United States of America 83, 4167-4171.

Rubinstein, M. P., Su, E. W., Suriano, S., Cloud, C. A., Andrijauskaite, K., Kesarwani, P., Schwartz, K. M., Williams, K. M., Johnson, C. B., Li, M., et al. (2015). Interleukin-12 enhances the function and anti-tumor activity in murine and human CD8(+) T cells. Cancer immunology, immunotherapy: CII 64, 539-549.

Sato, Y., and Rifkin, D. B. (1989). Inhibition of endothelial cell movement by pericytes and smooth muscle cells: activation of a latent transforming growth factor-beta 1-like molecule by plasmin during co-culture. J Cell Biol 109, 309-315.

Siegel, P. M., Shu, W., Cardiff, R. D., Muller, W. J., and Massague, J. (2003). Transforming growth factor beta signaling impairs Neu-induced mammary tumorigenesis while promoting pulmonary metastasis. Proceedings of the National Academy of Sciences of the United States of America 100, 8430-8435.

Stockis, J., Colau, D., Coulie, P. G., and Lucas, S. (2009). Membrane protein GARP is a receptor for latent TGF-beta on the surface of activated human Treg. European journal of immunology 39, 3315-3322.

Sunderkotter, C., Goebeler, M., Schulze-Osthoff, K., Bhardwaj, R., and Sorg, C. (1991). Macrophage-derived angiogenesis factors. Pharmacol Ther 51, 195-216.

Szepetowski, P., 011endorff, V., Grosgeorge, J., Courseaux, A., Birnbaum, D., Theillet, C., and Gaudray, P. (1992). DNA amplification at 11q13.5-q14 in human breast cancer. Oncogene 7, 2513-2517.

Tesseur, I., Zou, K., Berber, E., Zhang, H., and Wyss-Coray, T. (2006). Highly sensitive and specific bioassay for measuring bioactive TGF-beta. BMC cell biology 7, 15.

Tran, D. Q. (2012). TGF-beta: the sword, the wand, and the shield of FOXP3(+) regulatory T cells. J Mol Cell Biol 4, 29-37.

Tran, D. Q., Andersson, J., Wang, R., Ramsey, H., Unutmaz, D., and Shevach, E. M. (2009). GARP (LRRC32) is essential for the surface expression of latent TGF-beta on platelets and activated FOXP3+ regulatory T cells. Proceedings of the National Academy of Sciences of the United States of America 106, 13445-13450.

Wang, R., Kozhaya, L., Mercer, F., Khaitan, A., Fujii, H., and Unutmaz, D. (2009). Expression of GARP selectively identifies activated human FOXP3+ regulatory T cells. Proceedings of the National Academy of Sciences of the United States of America 106, 13439-13444.

Wang, R., Wan, Q., Kozhaya, L., Fujii, H., and Unutmaz, D. (2008). Identification of a regulatory T cell specific cell surface molecule that mediates suppressive signals and induces Foxp3 expression. PloS one 3, e2705.

Wang, R., Zhu, J., Dong, X., Shi, M., Lu, C., and Springer, T. A. (2012). GARP regulates the bioavailability and activation of TGFbeta. Molecular biology of the cell 23, 1129-1139.

Wu, S., Hong, F., Gewirth, D., Guo, B., Liu, B., and Li, Z. (2012). The molecular chaperone gp96/GRP94 interacts with Toll-like receptors and integrins via its C-terminal hydrophobic domain. The Journal of biological chemistry 287, 6735-6742.

Xie, L., Law, B. K., Aakre, M. E., Edgerton, M., Shyr, Y., Bhowmick, N. A., and Moses, H. L. (2003). Transforming growth factor beta-regulated gene expression in a mouse mammary gland epithelial cell line. Breast cancer research: BCR 5, R187-198.

Xu, J., Lamouille, S., and Derynck, R. (2009). TGF-beta-induced epithelial to mesenchymal transition. Cell research 19, 156-172.

Yu, Q., and Stamenkovic, I. (2000). Cell surface-localized matrix metalloproteinase-9 proteolytically activates TGF-beta and promotes tumor invasion and angiogenesis. Genes & development 14, 163-176.

Zhang, Y., Wu, B. X., Metelli, A., Thaxton, J. E., Hong, F., Rachidi, S., Ansa-Addo, E., Sun, S., Vasu, C., Yang, Y., et al. (2015). GP96 is a GARP chaperone and controls regulatory T cell functions. The Journal of clinical investigation 125, 859-869.

---

What is claimed is:

1. A recombinant polypeptide comprising an antibody VH domain comprising CDRs 1-3 of the VH domain of 4d3 (SEQ ID NOs: 1, 2, and 3).

2. A recombinant polypeptide comprising an antibody VL domain comprising CDRs 1-3 of the VL domain of 4d3 (SEQ ID NOs: 5, 6, and 7).

* * * * *